US012629054B2

(12) United States Patent
Mummy

(10) Patent No.: US 12,629,054 B2
(45) Date of Patent: May 19, 2026

(54) POSTURE MEASUREMENT SYSTEM FOR REALIGNMENT

(71) Applicant: Symmetry for Health, LLC, Folsom, CA (US)

(72) Inventor: Patrick Mummy, Folsom, CA (US)

(73) Assignee: Symmetry for Health, LLC, Folsom, CA (US)

( * ) Notice: Subject to any disclaimer, the term of this patent is extended or adjusted under 35 U.S.C. 154(b) by 385 days.

(21) Appl. No.: 18/388,508

(22) Filed: Nov. 9, 2023

(65) Prior Publication Data

US 2024/0148275 A1      May 9, 2024

Related U.S. Application Data

(60) Provisional application No. 63/424,042, filed on Nov. 9, 2022.

(51) Int. Cl.
| | |
|---|---|
| *A61B 5/11* | (2006.01) |
| *A61B 5/00* | (2006.01) |
| *A63B 21/00* | (2006.01) |
| *A63B 24/00* | (2006.01) |
| *A63B 71/06* | (2006.01) |

(52) U.S. Cl.
CPC .......... *A61B 5/1116* (2013.01); *A61B 5/0004* (2013.01); *A61B 5/1121* (2013.01); *A61B 5/706* (2013.01); *A63B 21/4037* (2015.10);

*A63B 24/0075* (2013.01); *A63B 71/0622* (2013.01); *A61B 2562/0219* (2013.01); *A63B 2230/62* (2013.01)

(58) Field of Classification Search
None
See application file for complete search history.

(56) References Cited

U.S. PATENT DOCUMENTS 7,335,167 B1 *   2/2008   Mummy .............. A61B 5/1071
600/595

* cited by examiner

*Primary Examiner* — Jay B Shah
(74) *Attorney, Agent, or Firm* — Mintz Levin Cohn Ferris Glovsky and Popeo, P.C.

(57) ABSTRACT

Methods, devices, and systems are described for a posture measurement system. The posture measurement system includes a plane alignment measurer having at least two arms and an angle sensor configured to determine a first posture angle at which the patient is tilted relative to a first plane of symmetry. The posture measurement system includes a plane alignment laser tool having at least two arms and a laser configured to generate focused light that is used to determine a second posture angle at which the patient is tilted relative to a second plane of symmetry. The posture measurement system includes a controller configured to generate a rehabilitation routine for correcting posture misalignments where rehabilitation routine is based on the first posture angle and the second posture angle.

20 Claims, 14 Drawing Sheets

100

210
Sagittal plane

220
Transverse
plane

230
Frontal plane

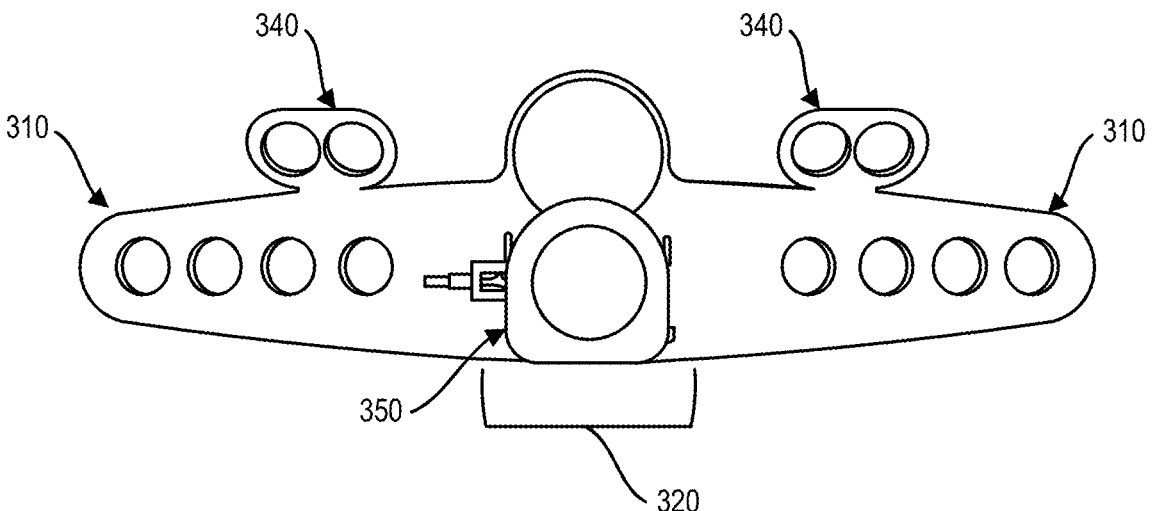
FIG. 3

350

420

410

350

430

600

610

ALIGNSMART

620

630

550

710

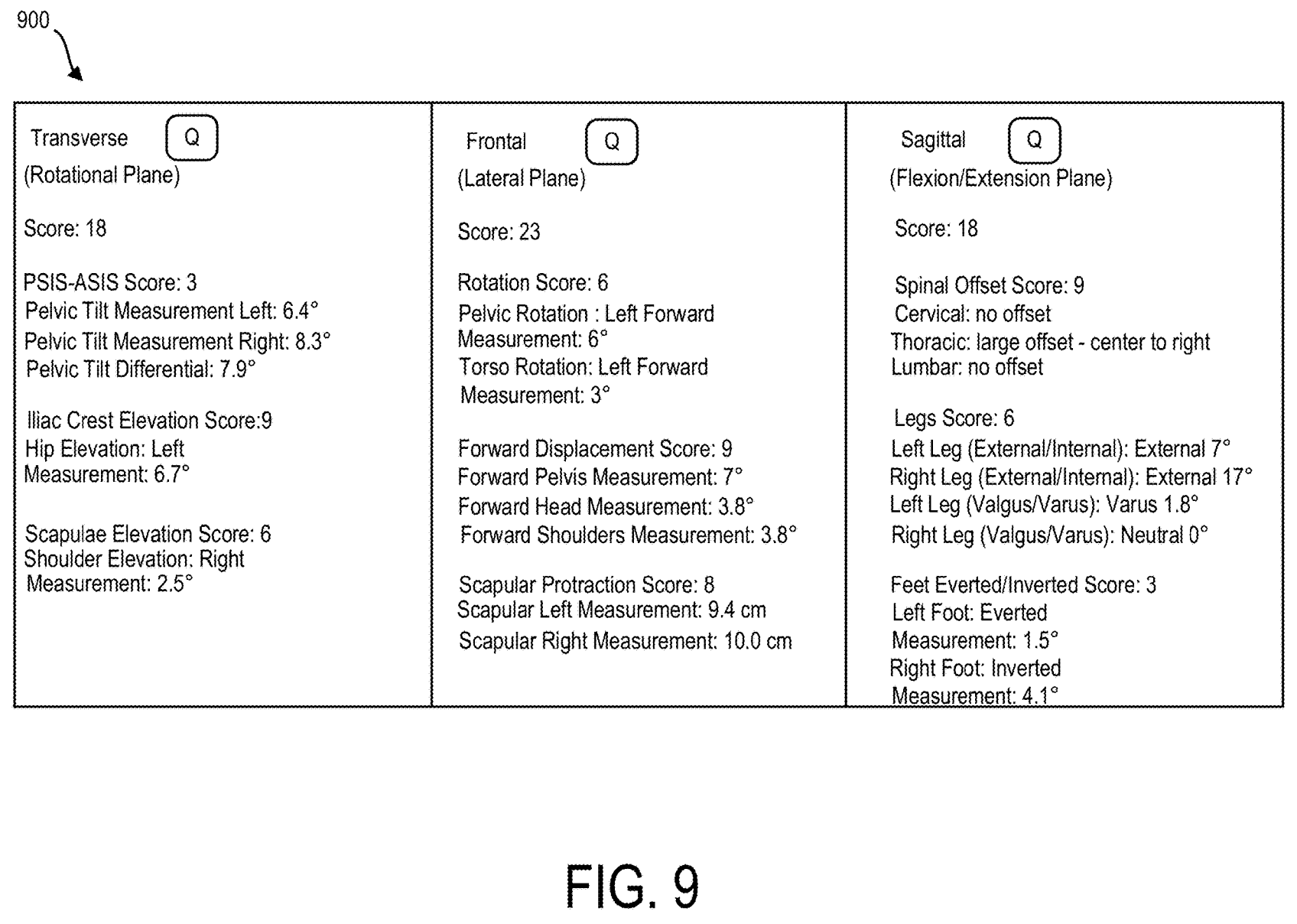

900

Transverse  [Q]
(Rotational Plane)

Score: 18

PSIS-ASIS Score: 3
Pelvic Tilt Measurement Left: 6.4°
Pelvic Tilt Measurement Right: 8.3°
Pelvic Tilt Differential: 7.9°

Iliac Crest Elevation Score:9
Hip Elevation: Left
Measurement: 6.7°

Scapulae Elevation Score: 6
Shoulder Elevation: Right
Measurement: 2.5°

Frontal  [Q]
(Lateral Plane)

Score: 23

Rotation Score: 6
Pelvic Rotation : Left Forward
Measurement: 6°
Torso Rotation: Left Forward
Measurement: 3°

Forward Displacement Score: 9
Forward Pelvis Measurement: 7°
Forward Head Measurement: 3.8°
Forward Shoulders Measurement: 3.8°

Scapular Protraction Score: 8
Scapular Left Measurement: 9.4 cm
Scapular Right Measurement: 10.0 cm Sagittal  [Q]
(Flexion/Extension Plane)

Score: 18

Spinal Offset Score: 9
Cervical: no offset
Thoracic: large offset - center to right
Lumbar: no offset Legs Score: 6
Left Leg (External/Internal): External 7°
Right Leg (External/Internal): External 17°
Left Leg (Valgus/Varus): Varus 1.8°
Right Leg (Valgus/Varus): Neutral 0°

Feet Everted/Inverted Score: 3
Left Foot: Everted
Measurement: 1.5°
Right Foot: Inverted
Measurement: 4.1°

FIG. 9

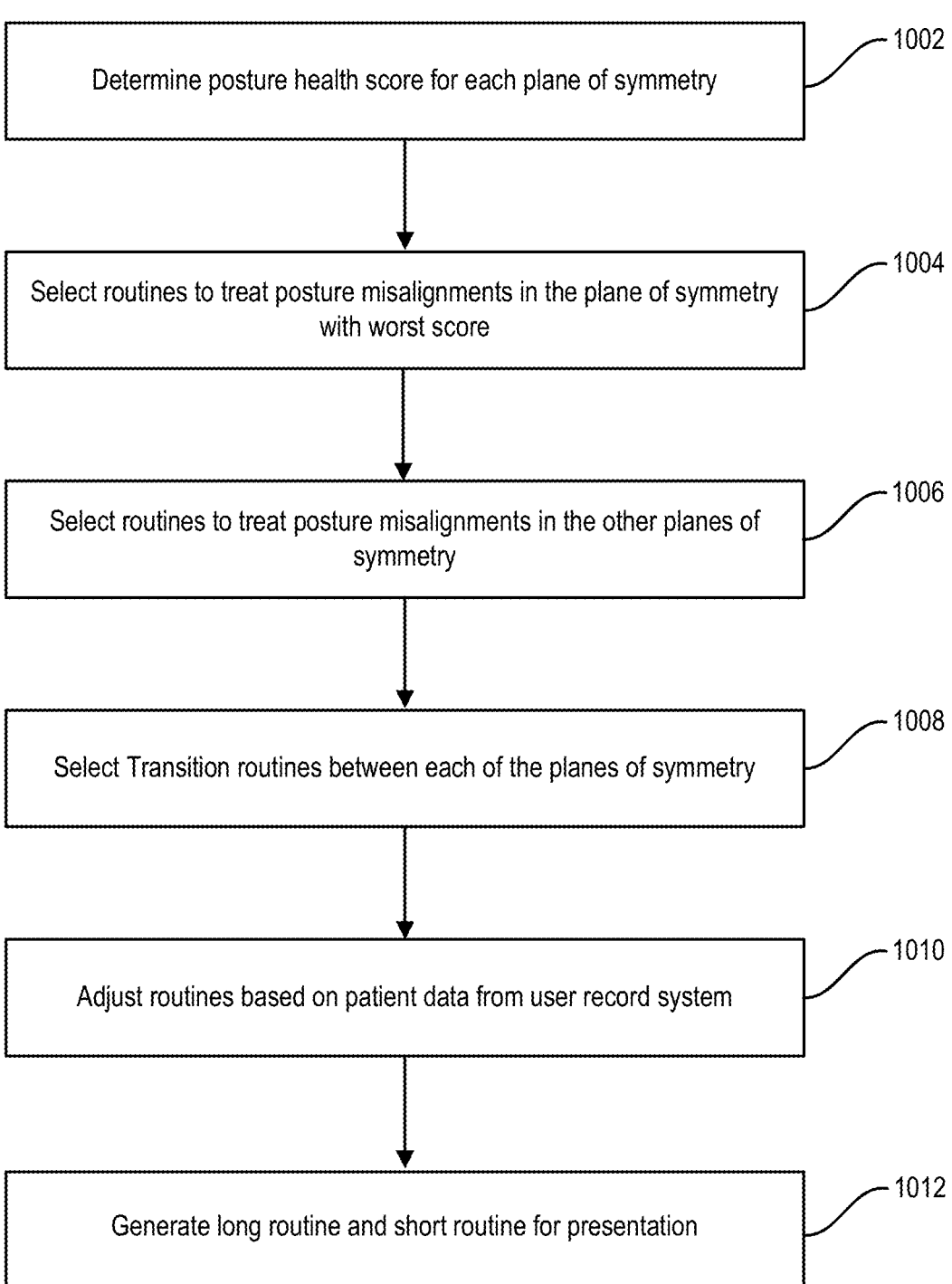

1002 — Determine posture health score for each plane of symmetry

1004 — Select routines to treat posture misalignments in the plane of symmetry with worst score 1006 — Select routines to treat posture misalignments in the other planes of symmetry 1008 — Select Transition routines between each of the planes of symmetry 1010 — Adjust routines based on patient data from user record system 1012 — Generate long routine and short routine for presentation

FIG. 10

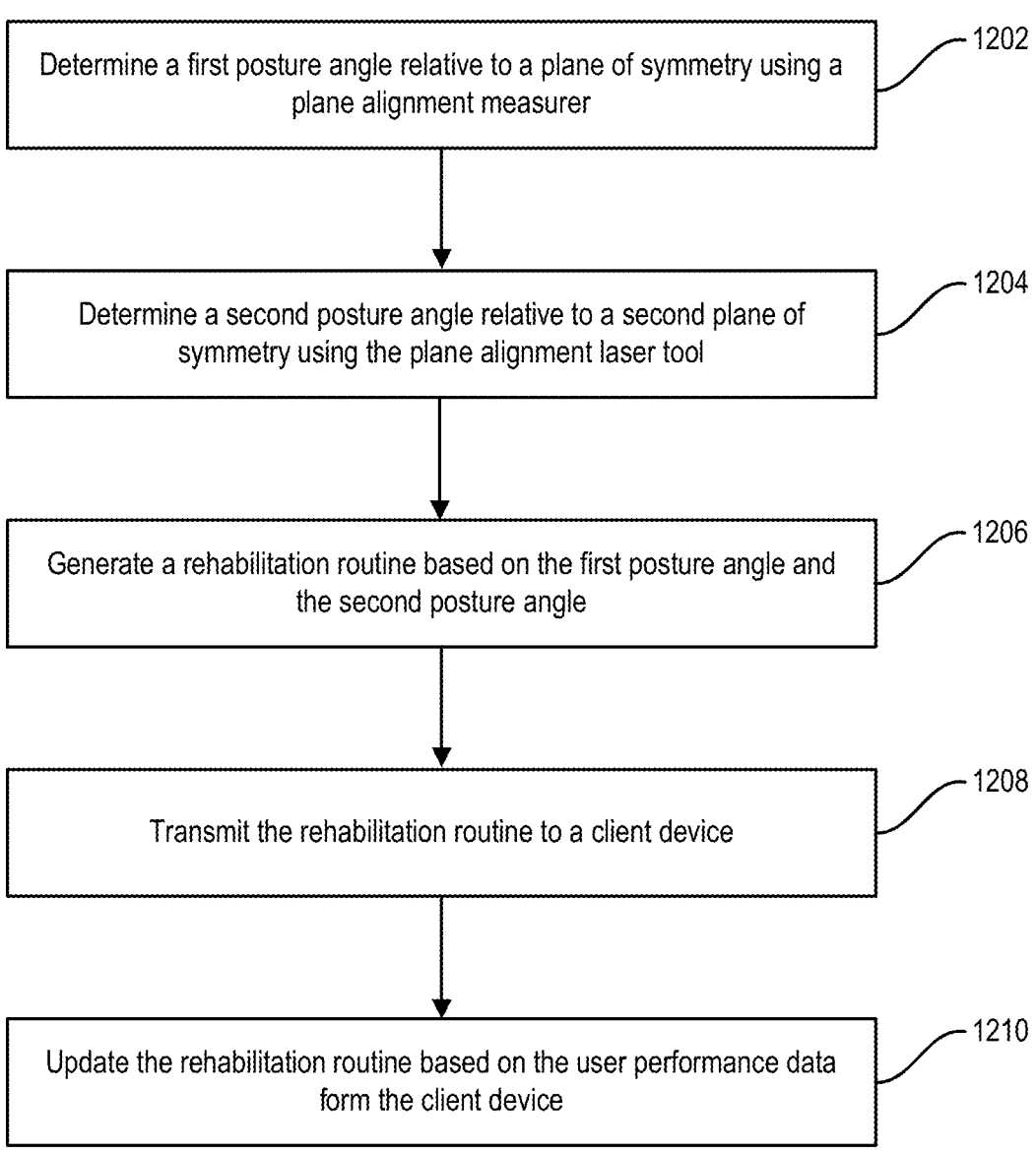

Determine a first posture angle relative to a plane of symmetry using a plane alignment measurer — 1202

Determine a second posture angle relative to a second plane of symmetry using the plane alignment laser tool — 1204

Generate a rehabilitation routine based on the first posture angle and the second posture angle — 1206

Transmit the rehabilitation routine to a client device — 1208

Update the rehabilitation routine based on the user performance data form the client device — 1210

FIG. 12

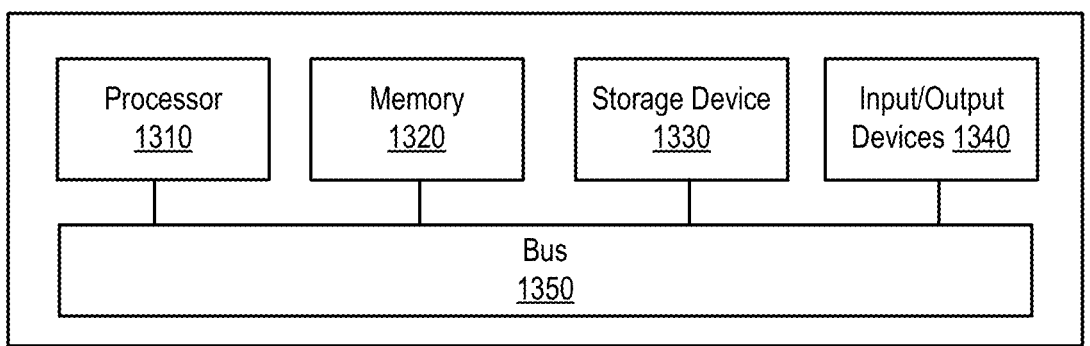
FIG. 13

POSTURE MEASUREMENT SYSTEM FOR REALIGNMENT

CROSS-REFERENCE TO RELATED APPLICATIONS

This application claims the benefit of priority from U.S. Provisional Application No. 63/424,042, entitled "Postural Measurement and Adaptive Alignment System", filed Nov. 9, 2022, which is incorporated herein in its entirety.

TECHNICAL FIELD

The present disclosure relates generally to posture wellness, and more particularly, to a posture measurement system for realignment.

BACKGROUND

Posture affects physical wellness, personal mobility, and the strength of the human body. Bad posture causes physical atrophy, reduced mobility, improperly utilized muscles, and the overcompensation of muscles that offset the improperly utilized muscles. Bad posture reduces the performance of the human body and the long-term wellness of the human body. While bad posture can be detected by visually assessing a patient, the early signs of bad posture are not detectable with a visual assessment alone. Deviations in posture are sometimes subtle and cannot be detected easily. Even small deviations can adversely affect posture and can lead to potentially damaging bodily compensations and dysfunctions. Sometimes, the patient does not realize there is a posture problem until the patient has chronic pain.

More problematic, the correction of bad posture requires rehabilitative exercises. Healthcare practitioners may be required to provide guidance to patients on correcting bad posture. Improper information and a misguided rehabilitation plan may further deteriorate the patient's condition. Healthcare personnel may be unable to prescribe a holistic rehabilitative exercise plan when multiple posture problems exist. As such, visual assessments of healthcare practitioners do not detect posture problems at early stages and selecting a set of rehabilitative exercises may be difficult for individuals with multiple posture misalignments.

SUMMARY

The present disclosure relates generally to the fields of posture wellness, and more particularly, to a digital measurement system for posture realignment.

In one aspect, disclosed herein are systems for measuring and realignment posture. The posture measurement system includes a plane alignment measurer having at least two arms and an angle sensor configured to determine a first posture angle at which the patient is tilted relative to a first plane of symmetry. The posture measurement system includes a plane alignment laser tool having at least two arms and a laser configured to generate focused light that is used to determine a second posture angle at which the patient is tilted relative to a second plane of symmetry. The posture measurement system includes a controller configured to generate a rehabilitation routine for correcting posture misalignments where rehabilitation routine is based on the first posture angle and the second posture angle.

In some variations, the plane alignment measurer includes a transmitter communicatively coupled to the controller. Additionally, the controller is further configured to receive the first posture angle transmitted by the plane alignment measurer. Further, the angle sensor includes at least one of an accelerometer or a gyroscope. In some variations, the arms are positioned to align with anatomical landmarks on the patient. In some variations, the controller is further configured to calculate a difference between the first posture angle and a first target posture angle, the first target posture angle being an ideal angle that the patient would be aligned with relative to the first plane of symmetry. Additionally, the controller is further configured to select a rehabilitative exercise to be performed in a supine position in response to the difference satisfying a misalignment threshold, the rehabilitative exercise to be included in the rehabilitation routine.

In some variations, the controller is further configured to calculate a difference between the first posture angle and a first target posture angle, the first target posture angle being an ideal angle that the patient would be aligned with relative to the first plane of symmetry. Additionally, the controller is further configured to determine the difference is less than a previously measured difference between a past posture angle and the first target posture angle. Further, the controller is further is further configured to adjust the rehabilitation routine based on the difference between the first posture angle and the first target posture angle in response to the difference being less than the previously measured difference between the past posture angle and the first target posture angle.

In some variations, the plane measurement system further includes a mat having a first side and a second side, the first side of the mat having a range of angles and the second side having crosshairs, the mat being configured to lay flat to allow the patient to stand on the mat with a plane of symmetry aligned with the crosshairs. Further, the plane alignment laser tool is further configured to focus light onto the mat in a line of focused light. Additionally, the second posture angle is determined by aligning the line of focused light from the laser onto the range of angles while the line is passing through the crosshairs.

In some variations, the plane measurement system further includes a client device configured to display a user interface for tracking goals and progress with the rehabilitation routine. Additionally, the controller is further configured to generate the user interface for presentation on the client device and add a new routine to the rehabilitation routine based on input from the client device, the input being indicative of an achieved goal and satisfactory progress with the rehabilitation routine.

In some variations, the controller is configured to determine that a third postural angle is needed from the plane alignment measurer. Further, the controller is configured to generate a prompt for presentation to an operator of the plane alignment measurer to take the third postural angle using the plane alignment measurer. Additionally, the controller is configured to update a postural health score in response to receiving the third postural angle. Further, the controller is configured to generate the rehabilitation routine based on the postural health score, the first posture angle, and the second posture angle.

In some variations, an ordering of the rehabilitation routine is determined based upon a severity of misalignments with respect to the first plane of symmetry and the second plane of symmetry. Further, the controller is configured to determine a first postural health score based on at least the first postural angle and a second postural health score based on the second posture angle. Additionally, the controller is configured to determine that a first set of rehabilitative exercises are to be added first to the routine based on the first postural health score being more severe than the second postural health score, the second postural health score being higher than the first postural health score prior to the weighting ratio being adjusted, the first set of rehabilitative exercises corresponding to the first plane of symmetry and a second set of rehabilitative exercises corresponding to the second plane of symmetry in response to adjusting the weighting ratio applied to first postural health score and the second postural health score. Further, the controller is configured to generate the rehabilitation routine with the first set of rehabilitative exercises to be performed before the second set of rehabilitative exercises.

BRIEF DESCRIPTION OF THE DRAWINGS

The embodiments herein may be better understood by referring to the following description in conjunction with the accompanying drawings in which like reference numerals indicate identically or functionally similar elements, of which:

FIG. 3 depicts an example of a plane alignment measurer configured to determine an angle of deviation from a plane of symmetry;

FIG. 9 depicts a posture health score chart providing a posture health score for each of the planes of symmetry based on the measurements taken using the plane alignment laser tool and the plane alignment measurer;

FIG. 10 depicts an example of a flowchart for prescribing a rehabilitation routine using the posture measurement data system;

FIG. 12 depicts an example of a flowchart for generating and updating a rehabilitation routine using measurements from the plane alignment measurer and the plane alignment laser tool; and FIG. 13 depicts a block diagram of a block diagram illustrating a computing system consistent with implementations of the current subject matter.

DETAILED DESCRIPTION

Figure 1:
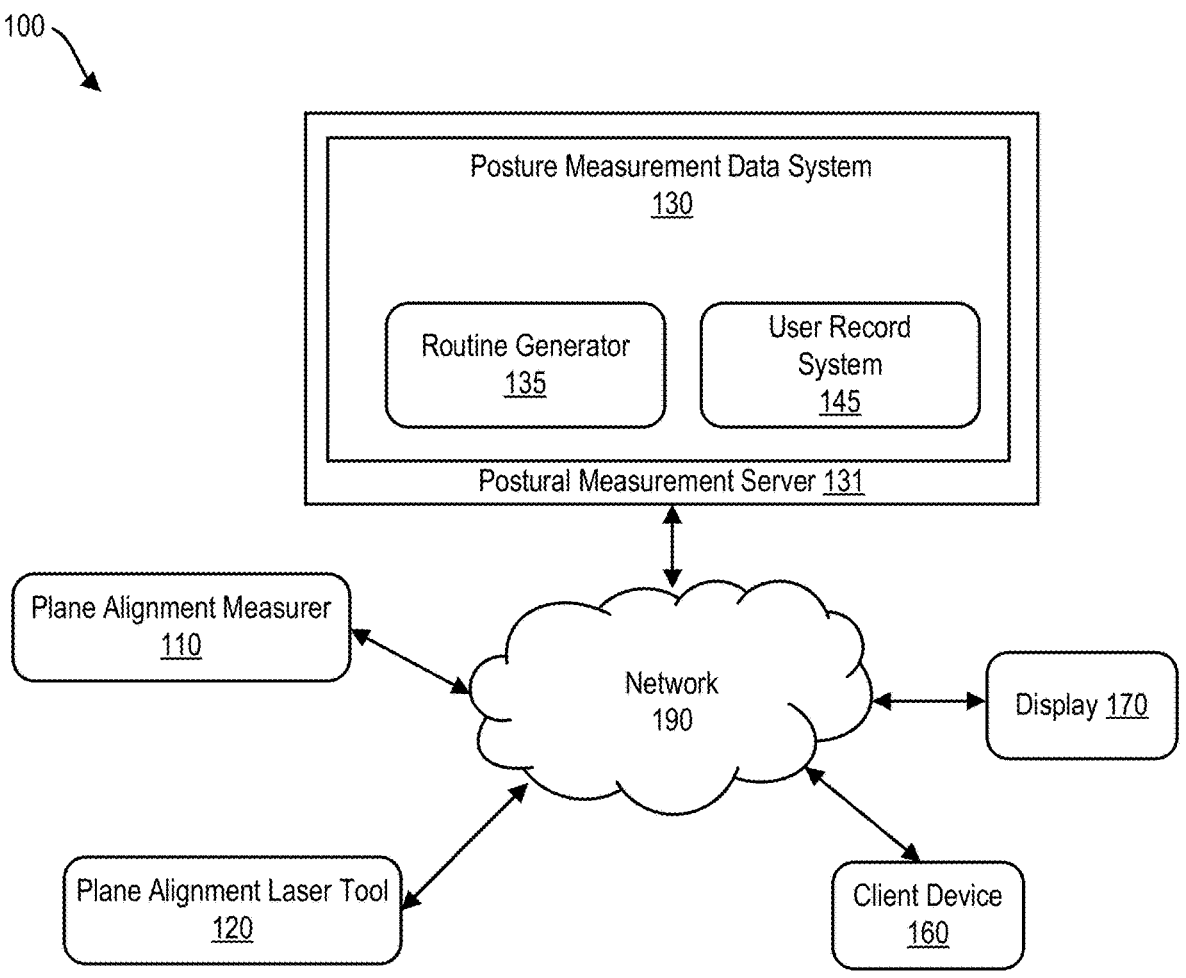
FIG. 1 depicts an example of a block diagram of a plane alignment measurer, a plane alignment laser tool, a display, a client device, and/or the posture measurement data system communicatively coupled via a network and/or via a direct device-device connection.

The methods, systems, and apparatuses described herein are for posture measurement systems for realignment. The posture measurement systems may be referred to as the posture alignment system. In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

The posture alignment system described herein provides hardware and software for measuring postural alignment and generating posture health scores and treatment for rehabilitation and realignment. The posture alignment system may include measurement tools to determine the angle of deviation from a postural plane of symmetry. The posture alignment system may determine a realignment exercise routine based on the angles of deviation for several different limbs and portions of the human body. The posture alignment system may prevent complications of bad posture and pain caused by posture misalignment. The posture alignment system may provide physical therapy and other rehabilitative therapy services. The posture alignment system may accelerate patient recovery, mobility, and various activities. To accomplish this, the posture alignment system may obtain accurate and consistent measurements more reliably than other healthcare professionals to provide optimized rehabilitative routines.

The posture alignment system may measure and provide postural alignment measurements at a greater level of attention than visual assessments from medical professionals. For example, the posture alignment system may measure small deviations of patient posture that would not otherwise be detectable with a visual assessment. These small deviations may be indicative of worsening postural alignment and poor posture habits that lead to patient pain and misalignment. The posture alignment system may take several measurements and look at the posture of a patient in three dimensions relative to at least three different planes of symmetry. In contrast, medical professionals may only identify greater posture deviations once posture misalignment has reached a later stage. Accordingly, the posture alignment system prevents misalignment, treats misalignment, and leads to greater quality of life for patients with postural misalignment.

According to the present disclosure, the posture alignment system may include a plane alignment measurer and a plane alignment laser tool that are configured to generate postural measurements for the posture alignment system. The posture alignment system may include a posture measurement data system that includes a routine generator and a user record system to generate a rehabilitative routine for the patient. The practitioner may be prompted to input data readings of the postural measurements through the display. Additionally, and/or alternatively, the display may output the rehabilitative routines generated by the posture alignment system for presentation to the patient. The patient may use a client device to access the rehabilitative routines and the client device may track patient performance and routine history through the client device. Additionally, and/or alternatively, the practitioner may access a portal through the client device to obtain details related to the patient in the user record system.

The postural alignment system may measure different parts of the body to determine the alignment with three different planes of symmetry or to determine whether the body is aligned with a target angle along the planes of symmetry. Other systems fail to take measurements along multiple planes of motion and combine the data to implement a rehabilitation program. Even if other systems use a camera to assess an angle at which the body is tilted, these measurements are not sufficiently accurate and do not evaluate the patient along multiple planes. The posture alignment system may correct this problem by taking multiple measurements along different angles and with the level of precision that is not achievable with a visual assessment or camera technology. The posture alignment system may prompt the measurement transmitters to take measurements and reject any measurements that are not properly calibrated with the plane of measurement. The posture alignment system may determine the portions of the body that are out of alignment at their earliest stages of deviation and may adapt to measuring different portions of the patient along the different planes of symmetry to detect the deviation. Other visual assessment systems may have difficulty in replicating prescriptions and replicating measurements to their subjective nature. The posture alignment system may determine the sequence in which measurements are taken and may update the sequence of measurements based on the patient's history of measurements throughout the assessment.

The prescribed rehabilitation exercise may correspond to a plane of symmetry. The rehabilitation exercise may correct a misalignment along a particular plane of symmetry. The posture alignment system may determine whether a routine is correcting a misalignment in a particular plane of symmetry over time. For example, the posture alignment system may determine that a rehabilitation routine or a combination of rehabilitation routines has not improved the patient misalignment. The posture alignment system may adapt the rehabilitation routine in view of other improvements that the patient has made since the start of treatment and may adjust the number of repetitions, or the types of rehabilitation exercises prescribed. The posture alignment system may refer to an algorithm, a chart, or a flowchart to update the rehabilitation exercise. The posture alignment system may request additional measurements to detect improvements to the patient's posture over time.

The posture alignment system solves technical problems associated with measuring postural misalignment in patients. Devices including accelerometers and/or digital gyroscopes may be configured to measure the postural misalignment relative to a plane and provide a higher degree of accuracy than otherwise achievable by humans or other hardware implementations. For example, imprecise human measurements may increase the risk of a false negative of improved posture, leading to delayed detection of postural misalignment in patients. In contrast, the postural measurement readings by the plane alignment measurer and the plane alignment laser tool may provide information to the posture alignment system to accurately detect posture alignments and misalignments, eliminating false negatives and early illness detection. The wrong rehabilitation exercises may compound the misalignment problems.

Additionally, the unique arrangement of the plane alignment measurer, the plane alignment laser tool, and the posture measurement server improves on existing hardware implementations. Existing hardware implementations may use visual assessments based on a sensor or camera. Such detached and two-dimensional measurements lead to inaccuracies as these devices are unable to consistently perceive and accommodate differences in user posture, limb angles, or changes in body size. In contrast, the posture alignment system may utilize a unique arrangement of the plane alignment measurer, the plane alignment laser tool, and a postural measurement server that is configured to measure patient posture. Further, the controller, when communicatively coupled to the plane alignment measurer and the client device, may be configured to factor in changes to user posture to obtain an accurate range of motion measurements. The unique combination of the plane alignment measurer, the plane alignment laser tool, and the exchange of data between these devices and the posture alignment system and the client devices of the posture alignment system may overcome the failure of older technologies.

The methods, systems, apparatuses, and non-transitory storage mediums described herein operate the posture alignment system to measure deviations in postural alignment and to determine an optimized rehabilitation routine optimized for the patient based on various deviations of postural alignment. The various exemplary embodiments also disclose a plane alignment measurer, the plane alignment laser tool, and a posture measurement server configured to measure posture misalignments relative to a plane of symmetry.

Referring to FIG. 1, illustrated is a block diagram of a posture alignment system 100 including plane alignment measurer 110, a plane alignment laser tool 120, a display 170, a client device 160, and/or the posture measurement data system 130 communicatively coupled via a network 190 and/or via a direct device-device connection. The network 190 may be a wired and/or wireless network including, for example, a public land mobile network (PLMN), a local area network (LAN), a virtual local area network (VLAN), a wide area network (WAN), the Internet, a short-range radio connection, for example, Bluetooth, a peer-to-peer mesh network, and/or the like.

The posture measurement data system 130 may be configured to receive measurements of plane deviations from the plane alignment measurer 110 and the plane alignment laser tool 120. The posture measurement data system 130 may prompt the plane alignment measurer 110 and the plane alignment laser tool 120 to take postural measurements of certain portions of the patient body. Additionally, and/or alternatively, the posture measurement data system 130 may display a prompt at the display to instruct the practitioner to perform a posture measurement using the plane alignment measurer 110 or the plane alignment laser tool 120. The posture measurement data system 130 may include a routine generator 135 and a user record system 145. Using the routine generator 135 and the user record system 145, the posture measurement data system 130 may generate a rehabilitation routine for the patient to realign the patient posture to certain angles relative to a plane of symmetry. The posture measurement data system may send the rehabilitation routine to a client device 160 for presentation to the patient. The posture measurement data system 130 tracks patient progress through the client device 160.

The posture measurement data system 130 may be configured to transmit messages to the plane alignment measurer 110, the plane alignment laser tool 120, the client device 160, and the interactive display 170. For example, the posture measurement data system 130 may determine that an additional measurement is needed to assess the patient posture. The posture measurement data system 130 may transmit a message to the plane alignment measurer 110 to take a measurement of the patient posture at a particular part of the body. The plane alignment measurer 110 may be configured to transmit a message to the posture measurement data system 130 with the angle of deviation relative to a plane. In another example, the posture measurement data system 130 may also transmit a rehabilitation routine to a client device.

The client device 160 may be a mobile device such as, for example, a smartphone, a tablet computer, a wearable apparatus, and/or the like. However, it should be appreciated that the client device 160 may be any processor-based device including, for example, a desktop computer, a laptop or mobile computer, a workstation, and/or the like. For example, via the client device 160, the user may be able to access rehabilitation routines and upload results to the posture measurement data system 130. The posture measurement data system 130 may configure certain parameters of the user record system 145, such as the location of a patient, a request for a medication, a drug schedule, and the like. Additionally, in some examples, via the client device 160, the user may configure patient information, patient conditions, patient progress, patient medications, and/or the like.

The display 170 may form a part of the posture measurement data system 130 or may be separately coupled as part of the client device 160. The display 170 may also include a user interface. The user interface may form a part of a display 170 screen of the display 170 that presents information to the user (e.g., a clinician, a patient, or caregiver for the patient) and/or the user interface may be separate from the display 170. For example, the user interface may be one or more buttons, or portions of the display 170 that is configured to receive an entry from the user.

The posture measurement data system 130 may include one or more databases, providing physical data storage within a dedicated facility and/or being locally stored on the postural measurement server 131 and/or the client device 160. Additionally, and/or alternatively, the posture measurement data system 130 may include cloud-based systems providing remote storage of data in, for example, a multi-tenant computing environment and/or the like. The posture measurement data system 130 may also include non-transitory computer-readable media.

The posture measurement data system 130 may include a user record system 145 and a routine generator 135. The user record system 145 may include patient details relating to a patient weight, a patient flexibility, a patient center of mass, patient dimensions, patient conditions, patient medications, and/or the like. The user record system 145 may store a plurality of electronic medical records, each of which includes the patient's medical history, one or more patient parameters (including posture measurements and past rehabilitation routines), one or more routine protocols (including limitations for performing certain routines), and/or the like. The routine generator 135 may generate a list of rehabilitative movements to be performed by the patient that are necessary to realign the patient to a target posture or angle of deviation. The routine generator 135 may prescribe an exercise for improving the patient posture health score. In some embodiments, the routine generator 135 may generate the routine based on the name of the routine and the intended effects of the routine. The routine generator 135 may determine an exercise according to the posture health score for the plane of symmetry. The routine generator 135 may refer to a database to determine how each of the exercises improves the posture health score for any given posture plane.

The posture measurement data system 130 may include and/or be coupled to a postural measurement server 131, which may be a server coupled to a network, a cloud server, and/or the like. The plane alignment measurer 110, the plane alignment laser tool 120, and/or the client device 160 may wirelessly communicate with the postural measurement server 131. The postural measurement server 131, which may include a cloud-based server, may provide and/or receive data and/or instructions from the posture measurement data system 130 to the posture measurement data system 130 and/or the client device 160, to implement one or more features of the posture alignment system 100 consistent with embodiments of the current subject matter. Additionally, and/or alternatively, the posture measurement data system 130 may receive data (e.g., patient information, information characterizing a health condition of a patient, medication information, posture measurements, and/or the like) from the plane alignment measurer 110, and/or the client device 160.

Figure 2:
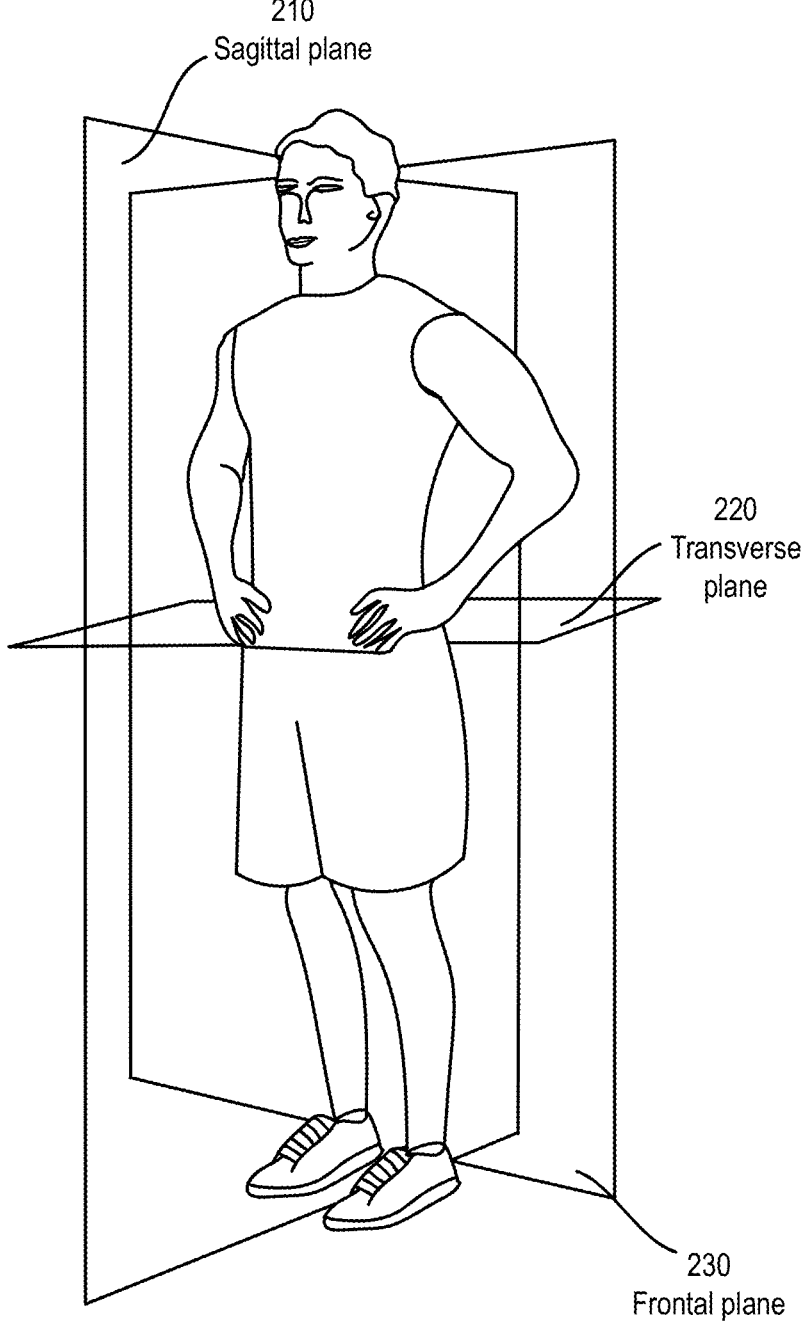
FIG. 2 depicts an exemplary diagrams of planes, including the frontal plane, the transverse plane, and the sagittal plane.

Referring to FIG. 2, illustrated is an exemplary diagram of planes of symmetry, including the sagittal plane 210, the transverse plane 220, and the frontal plane 230.

The sagittal plane 210 may be vertical and extend from the front side of the patient to the backside of the patient. The sagittal plane 210 may run in the same direction as the sagittal suture of the skull. The sagittal plane 210 may also be referred to as an anterior/posterior plane or viewed from an anterior or posterior perspective. The sagittal plane 210 may divide the body into a left side and a right side, where the left side is equal to the right side. The posture alignment system 100 may take measurements of the patient's anterior or posterior view to obtain information about the sagittal plane 210. Exercises for the sagittal plane 210 may include abdominal crunches to cobra, core abdominal muscles to hamstring stretch, hamstring stretch to heel slides, kneeling clock to prone knee press, prone leg curls to sitting knee lifts, sitting knee sequence to wall sit.

The frontal plane 230 may be vertical and extend from side to side. The frontal plane 230 may extend in the same direction as the coronal suture of the skull. The frontal plane 230 may divide the body into an anterior and posterior portion. The frontal plane 230 may be viewed mainly from the side or lateral perspective. The frontal plane 230 may also be referred to as the coronal plane or the lateral plane. Exercises for the frontal plane 230 may include a pelvic bridge to shoulder sequence, inverted splits to pec stretch, elevated blocked floor to intercostal stretch, and ankle/knee press (no lift) to elbow rotations.

The transverse plane 220 may be horizontal and may divide the body into an upper portion and a lower portion. The upper portion of the transverse plane 220 may be referred to as the cranial portion, and the lower portion of the transverse plane 220 may be referred to as the caudal portion. The postural alignment system may take measurements at the frontal plane 230, at the side.

In some embodiments, the sagittal plane 210 refers to a plane approximately intersecting the left and right sides of the body. The frontal or coronal plane 185 refers to a plane approximately intersecting the front and back sides of the body. The transverse plane 220 refers to a plane approximately intersecting the upper and lower portions of the body. For purposes of collecting measurements of the body to be entered into the system, an ideal anatomical position of the body is an erect posture, face forward, arms at sides, palms of hands forward with fingers and thumbs in extension. The correct posture position can serve as a reference for definitions and descriptions of body planes and movements. It is designed as the "zero" position for measuring joint motions for most of the joints of the human body.

Deviations of different body parts may indicate a deviation from a proper posture along a particular plane of symmetry. For example, feet that are either pronated or supinated indicate a postural misalignment along the sagittal plane 210. In another example, a hand forward or rounded more than the other is indicative of a postural misalignment along a frontal plane 230. In another example, a forward rotation of the pelvis or a protracted scapula is indicative of a postural misalignment along the frontal plane 230. In another example, one hip higher or a scapula elevated are indicative of a postural misalignment along the transverse plane 220. In another example, more space between an arm 310 and the torso relative to the other or an offset of the torso or head is indicative of a postural misalignment along the sagittal plane 210. In another example, the knees medial or external or one knee medial and the other external is indicative of a postural misalignment along the sagittal plane 210. In another example, the forward displacement of the pelvis, head, or knee hyperextension is indicative of a postural misalignment along the frontal plane 230.

Referring to FIG. 3, illustrated is a plane alignment measurer 110 configured to determine an angle of deviation from a plane of symmetry. The plane alignment measurer 110 may include at least an arm, an accelerometer and/or a gyroscope, and a transmitter. The plane alignment measurer 110 may include a central body 320 to which a housing 350 for the accelerometer and/or the gyroscope may be mounted. The housing 350 may be selectively coupled to the central body 320 of the plane alignment measurer 110. The housing 350 may also include a transmitter for transmitting patient measurement data to the posture measurement data system. The two arms may extend laterally from the central body 320. The two arms may be continuous with the central body 320 or may be selectively attached to the central body 320.

The plane alignment measurer 110 may include an accelerometer and/or a gyroscope configured to determine the angle at which the plane alignment measurer 110 is tilted. The plane alignment measurer 110 may be placed on a portion of the patient's body to determine the deviation from at least one of a sagittal plane 210, a transverse plane 220, and a frontal plane 230. The accelerometer and/or gyroscope may use the use the positioning, the balance, and/or the angle of the two arms to determine the angle of deviation relative to a plane. In some embodiments, the accelerometer and/or the gyroscope may determine whether the angle of deviation is from the frontal plane 230, the sagittal plane 210, or the transversal plane based on the orientation and the positioning of the plane alignment measurer 110. In some embodiments, the plane may be any plane in the x, y, or z direction. The plane alignment measurer 110 may be calibrated with one of the planes to determine the tilt, angle, or positioning of the arms relative to the plane. The practitioner may set the calibration of the plane alignment measurer 110 by pressing a button 420 when the arms are even with one along the plane or perpendicular to the plane.

The plane alignment measurer 110 may include two arms configured to connect at the central body 320 that supports the housing 350 with the accelerometer and/or the gyroscope. The arms may be flexible to allow the arms to be held flush against the portion of the patient body. The ends of the arms may be held flush against the portion of the patient body. Each arm 310 of the plane alignment measurer 110 may include finger rings to provide stability when conducting the measurement. The plane alignment measurer 110 may include a cutout 410 at the end of the arms to provide stability in holding the plane alignment measurer 110 flush against the portion of the body. In some embodiments, each of the arms includes an upper support 340 having index finger rings. The upper support 340 may be coupled to the upper side of the arms and may be coupled at an angle to the arms to support the stability of the tool during measurements. The arms may be moved in an up-and-down motion between the landmarks at the portion of the patient body until the same or a similar point of each landmark has been located. Each arm 310 may be held between a thumb and forefinger, with either an index finger or middle finger placed on the end of the arm 310 to provide stability when conducting the measurements.

The plane alignment measurer 110 may be placed on a portion of the patient's body having symmetrical features. For example, the hip may have symmetrical features, and the plane alignment measurer 110 may be placed on the left side and the right side of the hip. In another example, the neck may have symmetrical features and the plane alignment measurer 110 may be placed at the back of the neck. The plane alignment measurer 110 may be placed on a portion of the patient body where the center body of the plane alignment measurer 110 aligns with a plane. For example, the side of the abdomen may intersect with the frontal plane 230. The center body of the plane alignment measurer 110 may be placed at the side of the abdomen that intersects with the frontal plane 230.

The plane alignment measurer 110 may include a housing 350 with a gyroscope or an accelerometer. The gyroscope and/or accelerometer may determine the angle at which the arms are tilted relative to the central body 320. The gyroscope and/or accelerometer may be coupled to a display and a computer memory. The display may present the measurements of the gyroscope and/or accelerometer representative of the angle at which the arms are tilted relative to the central body 320 or the plane. The memory may store the measurements of the gyroscope and/or accelerometer representative of the angle at which the arms are tilted relative to the central body 320 or the plane.

The plane alignment measurer 110 may include a transmitter. The transmitter may be configured to communicatively couple to the posture measurement data system. The transmitter may be configured to transmit the deviation angles from one of the planes to the posture measurement data system. In some embodiments, the plane alignment measurer 110 may include a receiver to indicate that the measurements were successfully transmitted. In some embodiments, the housing 350 may include a display to present a prompt of a measurement to be taken using the plane alignment measurer 110.

Figure 4B:
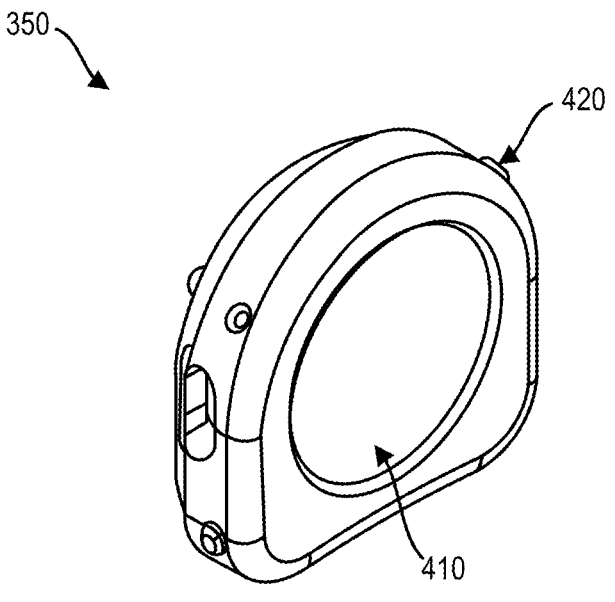
FIG. 4B depicts a side view of a housing to be mounted to the plane alignment measurer.
Figure 4A:
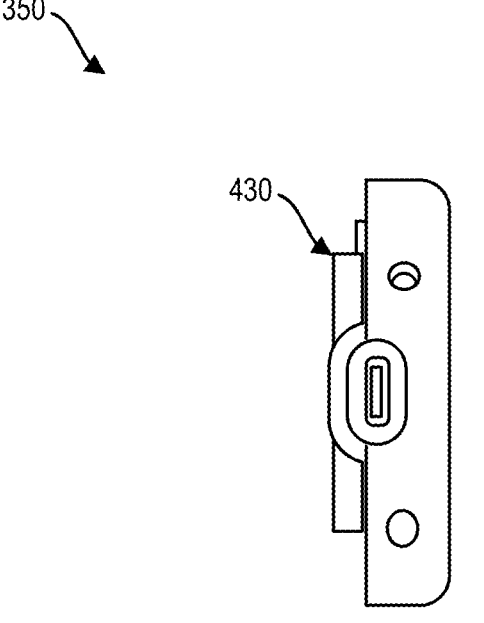
FIG. 4A depicts an angled view of a housing to be mounted to the plane alignment measurer.

Referring to FIG. 4A, illustrated is an angled view of a housing 350 to be mounted to the plane alignment measurer 110. The housing 350 may include a coupling interface, a button 420, and a cutout 410.

The housing 350 may include a cutout 410 for placing a computing device configured to transmit messages to the posture measurement data system. The computing device may include the gyroscope and/or the accelerometer. The computing device may be coupled to a display that is configured to display an image through the cutout 410. The computing device may present data measurement readings through the display.

The housing 350 may also include mating connector 430 or a magnet for coupling to the central body 320 of the plane alignment measurer 110. The mating connector 430 may be male connectors configured to project outside of the laser housing 550 to be received at the female connects at the plane alignment laser tool 120. In some embodiments, the mating connector 430 may be female connectors with apertures that are configured to receive male connectors at the plane alignment laser tool 120. The magnet may be configured to couple to a metal plate of the central body 320. The housing 350 may include a metal plate configured to be coupled to a magnet at the central body 320. The button 420 may be configured to hold a measurement taken by the accelerometer and/or the gyroscope. In some embodiments, the button 420 may be configured to transmit the measurement to the posture measurement data system. The USB port may be configured to recharge the computing device that is configured to transmit measurements to the posture measurement data system or display the data measurement readings.

Referring to FIG. 4B, illustrated is a side view of a housing 350 to be mounted to the plane alignment measurer 110.

Figure 5:
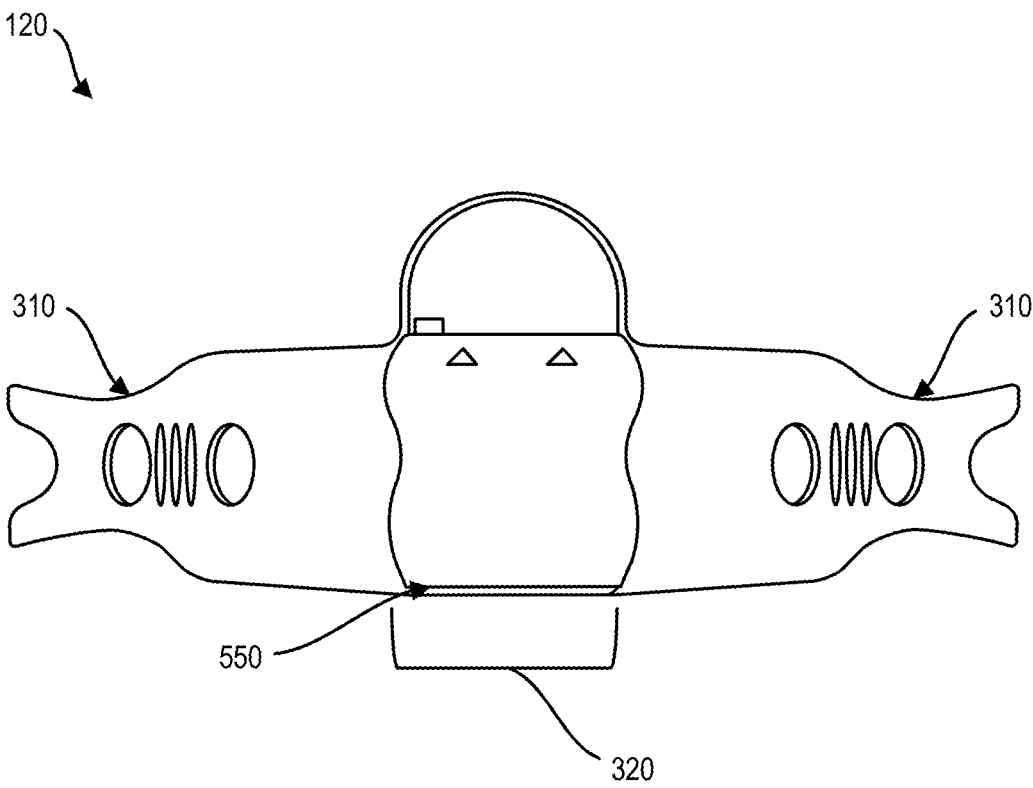
FIG. 5 depicts an example of a plane alignment laser tool configured to determine an angle of deviation from a plane of symmetry.

Referring to FIG. 5, illustrated is a plane alignment laser tool 120 configured to determine an angle of deviation from a plane of symmetry. The plane alignment laser tool 120 may include two arms, a laser, and a transmitter. The plane alignment laser tool 120 may include a central body 320 to which a laser housing 550 for the laser may be mounted. The laser housing 550 may be selectively coupled to the central body 320 of the plane alignment laser tool 120. The laser housing 550 may also include a transmitter for transmitting patient data to the alignment data system. The at least two arms may extend laterally from the central body 320. The two arms may be continuous with the central body 320 or may be selectively attached to the central body 320.

The plane alignment laser tool 120 may include a laser configured to project focused light outward from the housing 350. The focused light may be channeled into a line. The line created by the focused light may be used to determine the angle at which the plane alignment laser tool 120 is tilted or angled relative to a plane. The plane alignment laser tool 120 may be placed on a portion of the patient's body to determine the deviation from at least one of a sagittal plane 210, a transverse plane 220, and a frontal plane 230. The laser may use the positioning and the angle of the two arms to determine the tilt of the plane alignment laser tool 120 relative to a plane. The laser may be configured to project focused light away from the laser housing 550 onto a mat. The mat 600 may include a range of angles 610 across a dial. The angle at which the laser light shines on the range of angles 610 is representative of the angle at which the plan alignment tool is tilted. The distance between the mat 600 and the laser may be adjusted to accurately measure the angle at which the plane alignment laser tool 120 is tilted relative to the plane. In some embodiments, the plane alignment laser tool 120 may be configured to determine the angle at which the arms are tilted relative to the sagittal plane 210, the frontal plane 230, or the transversal plane. In some embodiments, the plane may be any plane in the x, y, or z direction. In some embodiments, the laser may be calibrated so that the focused light projected by the laser is emitted in a direction perpendicular to the arms of the plane alignment laser tool 120.

The plane alignment measurer 110 may include a camera coupled to the housing 350 configured to determine where the emitted focused light lands on the range of angles 610 on the mat. The camera may determine the angle among the range of angles 610 that the emitted focused light reaches. In some embodiments, the angling of the camera and/or the laser may determine whether the angle of deviation is from the frontal plane 230, the sagittal plane 210, or the transversal plane. The computing device coupled to the camera may transmit the angle of deviation to the posture measurement data system.

The plane alignment laser tool 120 may include two arms configured to connect at the central body 320 that supports the laser housing 550. The arms may be flexible to allow the arms to be held flush against the portion of the patient body. The ends of the arms may be held flush against the portion of the patient body to obtain the posture measurements. Each arm 310 of the plane alignment laser tool 120 may include finger rings to provide stability when conducting the measurement. The plane alignment laser tool 120 may include a cutout 410 at the end of the arms to provide stability in holding the plane alignment laser tool 120 flush against the portion of the body. In some embodiments, each of the arms includes an upper support 340 having index finger rings. The upper support 340 may be coupled to the upper side of the arms and may be coupled at an angle to the arms to support the stability of the tool during measurements. The arms may be moved in an up-and-down motion between the landmarks at the portion of the patient body until the same or a similar point of each landmark has been located. Each arm 310 may be held between a thumb and forefinger, with either an index finger or middle finger placed on the end of the arm 310 to provide stability when conducting the measurements.

The plane alignment laser tool 120 may be placed on a portion of the patient's body having symmetrical features. For example, the hip may have symmetrical features, and the plane alignment laser tool 120 may be placed on the left side and the right side of the hip. In another example, the neck may have symmetrical features, and the plane alignment laser tool 120 may be placed at the back of the neck. The plane alignment tool may be placed on a portion of the patient body where the center body of the plane alignment laser tool 120 aligns with a plane. For example, the side of the abdomen may intersect with the frontal plane 230. The center body of the plan alignment tool may be placed at the side of the abdomen that intersects with the frontal plane 230.

The plane alignment laser tool 120 may include a laser housing 550. The laser housing 550 may assist with determining the angle at which the arms are tilted relative to the central body 320. The laser may be coupled to a computing device with a display, a camera, and a transmitter. The camera may determine the angle among the range of angles 610 at the mat 600 that the emitted focused light reaches. The display may present the angle of deviation determined by the camera. The transmitter may be configured to send the angle determined by the camera to the posture measurement data system.

Figure 6:
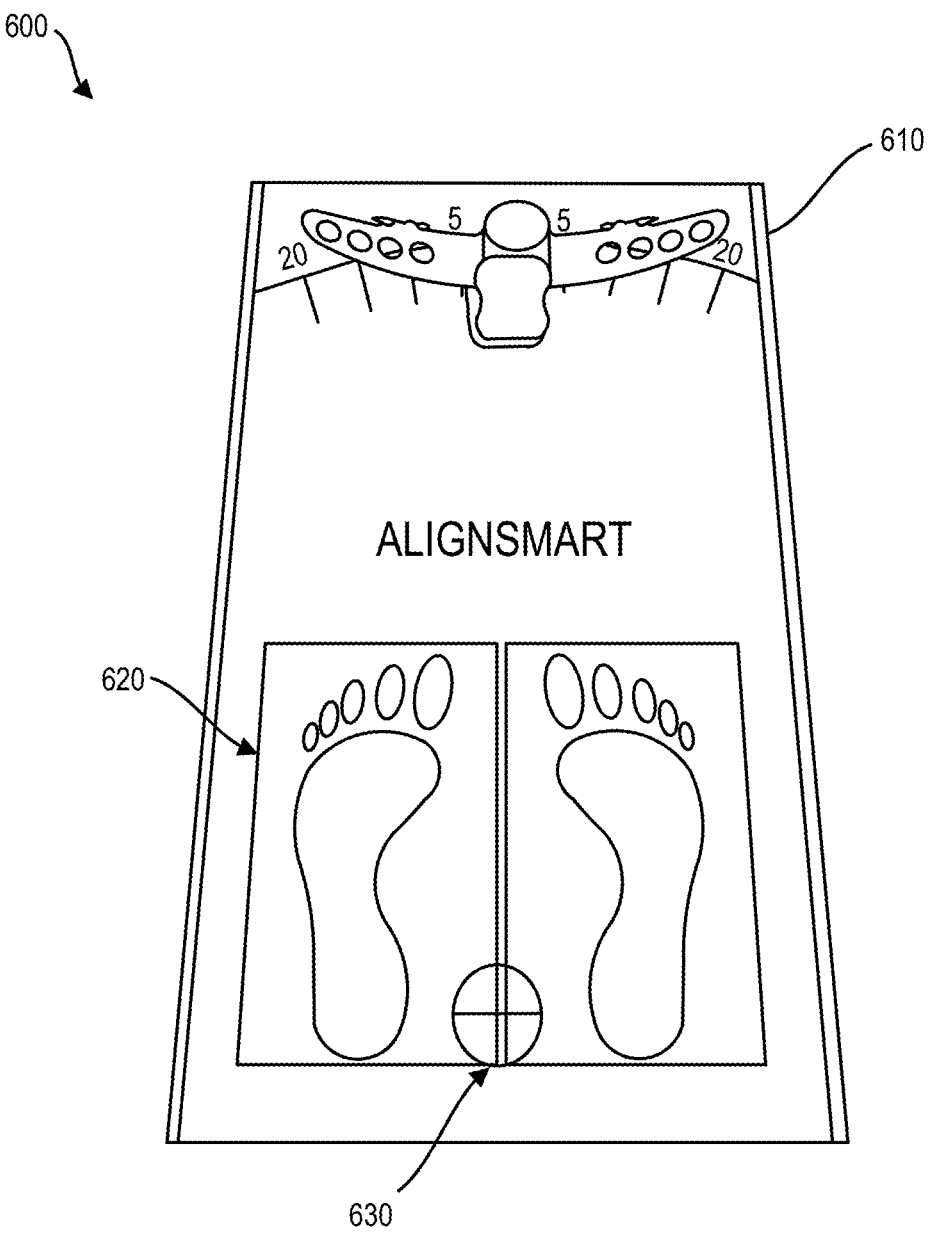
FIG. 6 depicts an example of a mat for assisting the plane alignment laser tool with determining the angle of deviation along a plane of symmetry.

Referring to FIG. 6, illustrated is a mat 600 for assisting the plane alignment laser tool 120 with determining the angle of deviation along a plane of symmetry. The mat 600 may include a dial representative of a range of angles 610, a cutout 410 for a foot placement section 620, and calibration crosshairs 630. The calibration crosshairs 630 and the dial representative of the range of angles 610 may be placed on opposite sides of the mat. The calibration crosshairs 630 may be situated between each of the foot placement section 620. The range of angles 610 may have the 0-degree angle mark aligned with the calibration crosshairs 630 in the longitudinal direction. The laser from the plane alignment laser tool 120 may be configured to project focused light toward the mat.

The dial representative of the range of angles 610 may be used to determine the angle of deviation along a plane. The laser may shine along the dial to indicate at which angle the plane alignment laser tool 120 deviates from a plane. The laser may shine light in a line. The line projected by the laser may be aligned with the calibration crosshairs 630 at the bottom portion of the mat 600 while also reaching an angle of deviation at the dial. In some embodiments, the angle aligned with the line from the laser determines the angle of deviation along the plane when the line projected by the laser simultaneously passes through the calibration crosshairs 630. In some embodiments, whether the focused light emitted from the laser shines to the left or the right of the 0-degree angle indicates whether a portion of the body (e.g., knee or leg) is pronated or supinated.

The calibration crosshairs 630 may be aligned with the plane of symmetry for the portion of the patient body. In some embodiments, the patient may align a portion of the patient body through which the plane of symmetry crosses with the calibration crosshairs 630. For example, the index toe may be aligned with the calibration crosshairs 630 to determine the angle of deviation of a knee or leg. The line projected by the laser may be aligned with the portion of the patient's body with which the plane of symmetry is aligned while also reaching an angle of deviation at the dial. In some embodiments, the angle aligned with the line from the laser determines the angle of deviation along the plane when the line projected by the laser simultaneously passes through the portion of the patient's body with which the plane of symmetry is aligned.

Figure 7A:
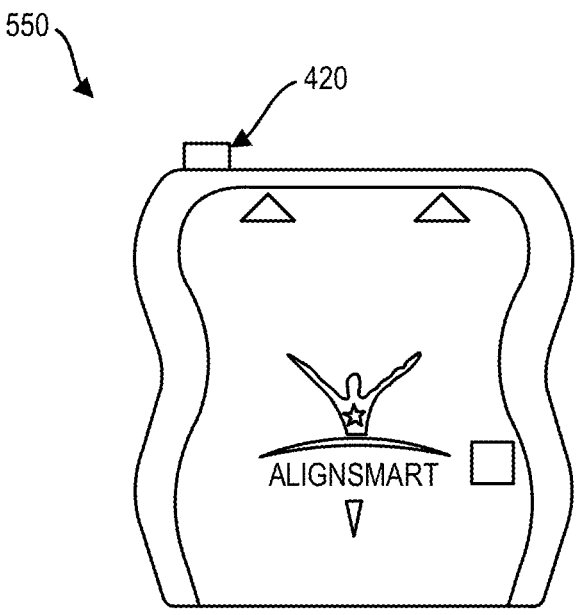
FIG. 7A depicts a view of a mountable laser configured to selectively couple to the center body of the plane alignment laser tool.
Figure 7B:
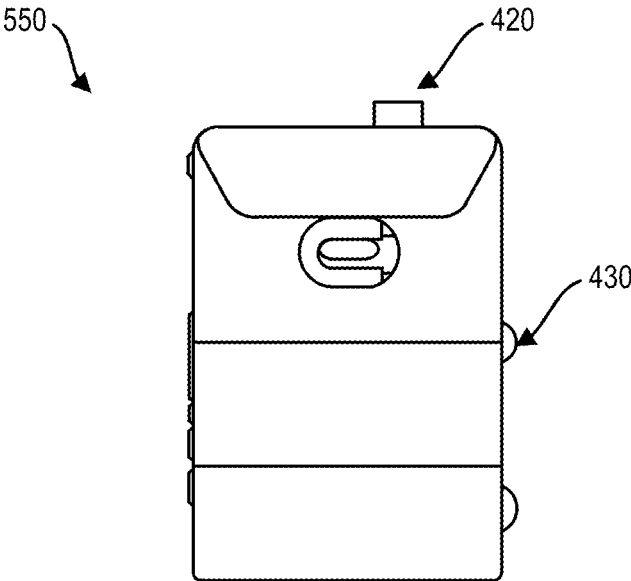
FIG. 7B depicts another view of the mountable laser configured to selectively couple to the center body of the plane alignment laser tool.

Referring to FIGS. 7A and 7B, illustrated is a mountable laser configured to selectively couple to the center body of the plane alignment laser tool 120. The mountable laser may include an opening for the laser lens and a button 420 to activate the laser. The mountable laser may also include mating connector 430. The mating connector 430 may be male connectors configured to project outside of the laser housing 550 to be received at the female connects at the plane alignment laser tool 120. In some embodiments, the mating connector 430 may be female connectors with apertures that are configured to receive male connectors at the plane alignment laser tool 120. The button 420 may be configured to activate the laser. The USB port may be configured to recharge the battery that is configured to power the laser.

Figure 7C:
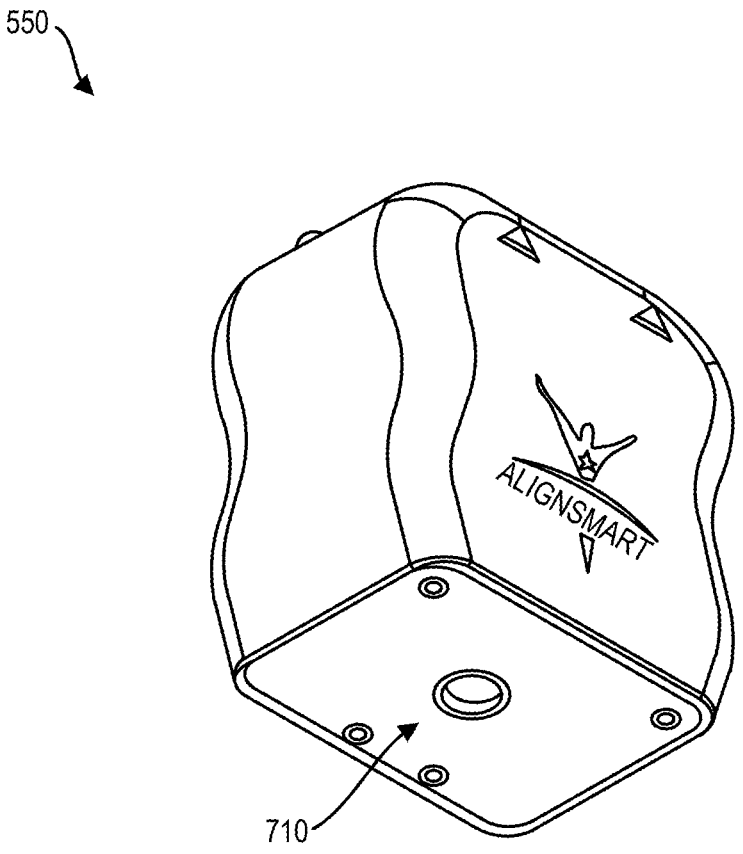
FIG. 7C depicts a bottom view of the mountable laser configured to selectively couple to the center body of the plane alignment laser tool.

Referring to FIG. 7C, illustrated is a bottom view of the mountable laser configured to selectively couple to the center body of the plane alignment laser tool 120. The laser lens may be situated at the bottom face 710 of the mountable laser. The laser may be oriented inside the mountable laser to project focused light from the bottom face 710 of the mountable laser.

Figure 8:
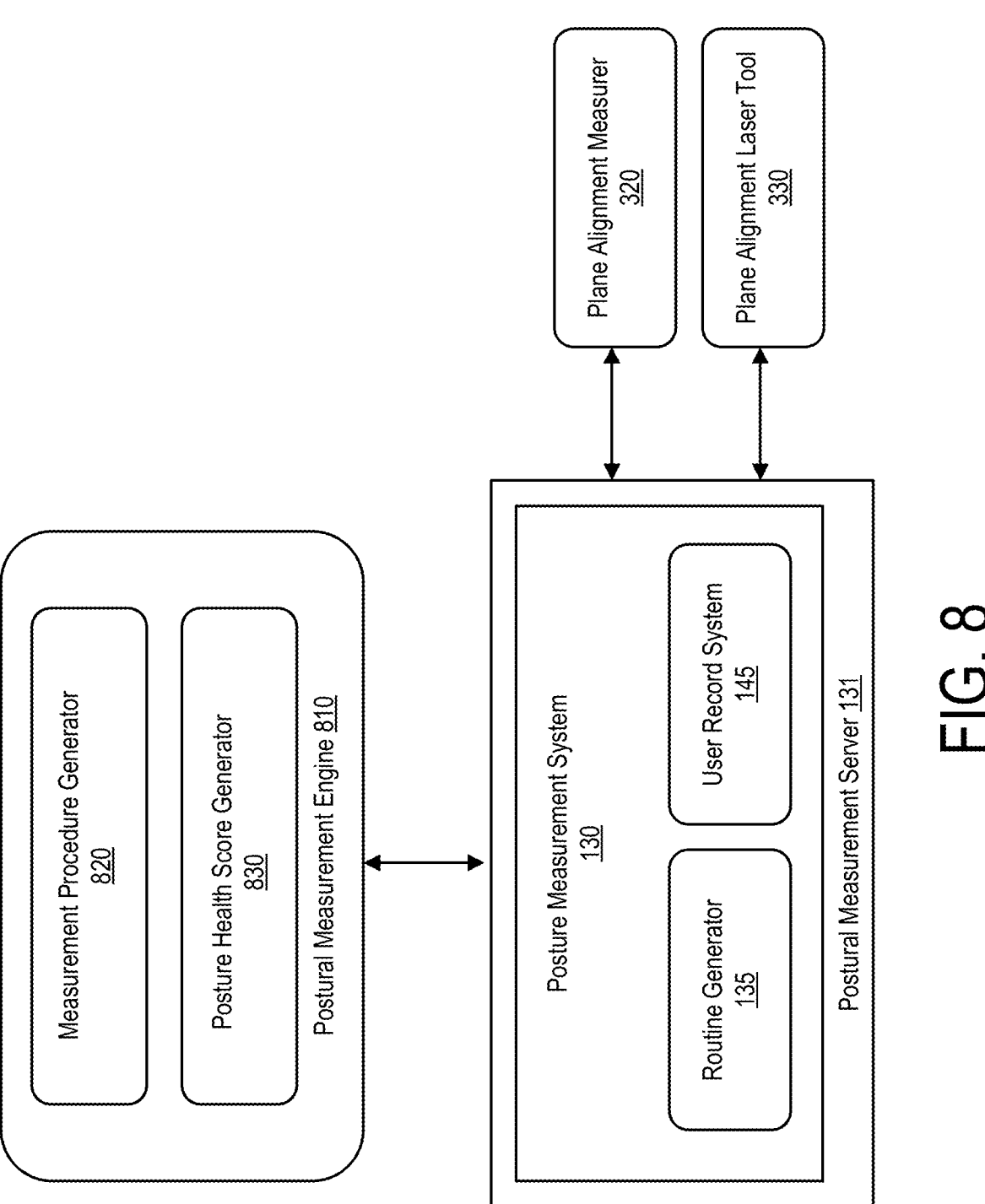
FIG. 8 depicts an example of a postural measurement engine configured to generate a posture health score for each of the planes of symmetry and to guide the practitioner through the posture measuring process.

Referring to FIG. 8, illustrated is a postural measurement engine 810 configured to generate a posture health score for each of the planes of symmetry and to guide the practitioner through the posture measuring process. The postural measurement engine 810 may include an algorithm representative of the relationships between the planes. The postural measurement engine 810 may be configured to guide the practitioner through the measurement process to gain an accurate cross-section across the planes and within each of the planes. The postural measurement engine 810 may include a measurement procedure generator 820 and a posture health score generator 830. The postural measurement engine 810 may be communicatively coupled with the posture measurement server to provide information to the routine generator 135 and the user record system 145.

The postural measurement engine 810 may be configured to generate a posture health score within each of the planes and the measurements within each plane and the factors associated as numerical values. The postural measurement engine 810 may apply a weighted algorithm to quantify the planar relationships. The weighted algorithm may determine the procedures used by the measurement procedure generator 820 to determine the most accurate measurements for determining the posture health score. The postural measurement may sort each of the measurements into transverse plane 220 measurements, frontal plane 230 measurements, or sagittal plane 210 measurements. The postural measurement engine 810 may determine any disparities in the measurements and determine the most correct process for eliminating the disparities.

The practitioner may input information related to the postural measurement engine 810 related to a patient's condition. The postural measurement engine 810 may determine whether the condition might affect the transverse plane 220, the frontal plane 230, or the sagittal plane 210. The postural measurement engine 810 may decide whether the condition affects any rotational, lateral, or medial movement. The postural measurement engine 810 may request measurements from the plane alignment measurer 110 and the plane alignment laser tool 120. The postural measurement engine 810 may request measurements that correspond to a plane that is potentially affected by the patient's condition. The postural measurement engine 810 may request measurements that would be indicative of any limitations of rotational, lateral, or medial movement. The measurement procedure generator 820 may consider the poor condition of the patient to recommend taking other measurements. For example, if the patient has difficulty with tight hamstrings, the measurement procedure generator 820 may require testing of the lumbar spine, groin, and hamstrings. The measurement procedure generator 820 may prompt the practitioner to measure these areas and input the findings. Additionally, and/or alternatively, the measurement procedure generator 820 may prompt the posture measurement data system 130 to have the areas of interest measured.

In some embodiments, the postural measurement engine 810 may be configured to determine the center of mass of the patient. The center of mass may be defined as the point at which the entire weight of the body may be concentrated, or a portion of weight of the body may be concentrated. In an ideally aligned posture in an adult patient, the center of gravity is slightly anterior to the first or second sacral segment. With respect to a symmetry evaluation, the definition of the center of mass is the point where all three planes of motion intersect. The postural measurement engine 810 may factor the center of mass for the patient or the portion of the patient when selecting a plane by which the posture measurement data system determines an angle of deviation.

In some embodiments, the postural alignment system may ensure the body is aligned along the center of mass. The abdomen, head, neck, shoulders, limbs, and torso of the patient may have centers of mass. For example, the center of mass of the upper arm lies about two-thirds up from the elbow joint. The vertical line passing through each may be referred to as the line of gravity, and it can be within either the sagittal or frontal plane 230.

The postural alignment system increases the likelihood that the practitioner begins measuring and analyzing the patient in all three dimensions and/or along all three planes of symmetry. The drawbacks of pictures, apps, and visual assessments are that they are limited to two-dimensional views instead of three and the eyes are drawn only to what is perceived as the biggest posture deviation. But posture health must be comprehensive from all three dimensions—otherwise, the assessment is incomplete and correcting some posture issues may cause complications for other posture issues that went undetected during the original assessment. The postural alignment system may enable quantifying all the measurements needed to obtain a holistic assessment of patient posture. The postural measurement engine 810 may also recommend measurements depending on the relationship of each plane or the amount of patient compensations made during an exercise or the measuring process.

The posture health score may determine whether the patient has limited performance in the frontal plane 230, the transverse plane 220, or the sagittal plane 210 based on the transverse plane 220 measurements, the frontal plane 230 measurements, and the sagittal plane 210 measurements. The posture health score may first determine whether the transverse plane 220 measurements, the frontal plane 230 measurements, and the sagittal plane 210 measurements affect any rotational, lateral, or medial movement. For example, if one has an elevated ilium, then a deviation from the transverse plane 220 may be measured. In some embodiments, a static postural misalignment may compromise the dynamic movement of that plane of symmetry. The posture health score considers the dynamic movements that are limited based on the static postural misalignments. The posture health score predicts movement limitations and goes beyond traditional therapies that primarily focus on rehabilitating weak muscles.

The routine generator 135 may identify the plane of symmetry that requires the most attention for rehabilitative exercises and movements. The routine generator 135 may prescribe an exercise for improving the patient posture health score for a particular plane of symmetry. For example, the routine generator 135 may recommend a torso twist as a rotational exercise for improving the posture health score in the transverse plane 220. In some embodiments, certain words in an exercise name may indicate the plane that the exercise improves. For example, abduction or flexion may indicate the exercise is to be performed in a particular plane. The routine generator 135 may generate the routine based on the name of the routine and the intended effects of the routine. The routine generator 135 may determine an exercise according to the posture health score for the plane. The routine generator 135 may refer to a database to determine how each of the exercises improves the posture health score for any given posture plane.

The routine generator 135 may consider a patient condition when prescribing a routine. For example, if a client has poor flexibility in the hamstrings, then there are certain exercises that would not be a good fit for this patient due to the amount of range of motion that is required to adequately perform the exercise. The routine generator 135 may add or remove exercises from the generated routine based on the muscles affected by the patient's condition.

The routine generator 135 may determine the exercises and the order of the exercises based on the posture health scores. The routine generator 135 may determine that the exercises corresponding to the plane with the highest planar health score are to be prescribed first (in systems where a high planar health score indicates high deviations from ideal posture). The routine generator 135 may then prescribe the exercises corresponding to the other two planes of symmetry. The routine generator 135 may determine which exercises are to be prescribed based on a ratio between the planes. For example, the planar scores may be calculated based on a ratio and not necessarily on face value. If all planes are scored equal, then the routine generator 135 determines that the order of the routine would be transverse, then frontal, and finally sagittal. The routine generator 135 applies a weight to each plane based on potential compensations directly related to the number of landmarks measured in each plane. The routine generator 135 may determine the weighting based on the transverse plane 220 having fewer measured landmarks than the frontal plane 230, which has fewer landmarks than the sagittal plane 210.

The posture health score generator 830 may mathematically relate the numbers in all three planes of symmetry to weigh the measured misalignments in order of significance. The routine generator 135 may adjust the ratio weighting for each of the three planes (see Appendix). The routine generator 135 may determine that there will be a 1:1:1 ratio among the planes if the planar score difference between each plane is three points or less. Therefore, if the transverse plane 220 score is 21, the sagittal plane 210 score is 19, and the frontal plane 230 score is 22. As such, the order of the planes being addressed would still be transverse, followed by frontal, and then sagittal due to the overall weight distribution. Anything more than three points will then order the planes based on face value. This means that any static disparity in the transverse plane 220 will have a much higher compensation reaction than that of the sagittal plane 210. This may be due to the smaller number of attachments in that plane.

The posture health score generator 830 may adjust the ratio weighting of each of the three planes according to the score of the iliac crest or the PSIS-ASIS measurements in the transverse plane 220 (see Appendix). The posture health score generator 830 may adjust the ratio so that the weighting addresses the transverse plane 220 first in response to the iliac crest or the PSIS-ASIS measurement satisfying a threshold. For example, even if the posture health score generator 830 determines that the iliac crest score is lower (i.e., better) than the other planes, the posture health score generator 830 may adjust the weight of the ratio for the transverse plane 220 higher than the other planes in response to the iliac crest satisfying the threshold. This is due to the high effect any large disparity in the transverse plane 220 will have on the other planes. If this large disparity is not addressed first in a routine, then all other corrections may not be as effective.

The measurement procedure generator 820 may select the measurements to be taken within each plane. Once the measurement procedure generator 820 determines the most troublesome planes, the measurement procedure generator 820 may determine the order of measurements to be taken within each plane. The measurement procedure generator 820 may follow a predetermined order within a given plane. For example, the measurement procedure generator 820 may determine that the PSIS-ASIS should be measured first, followed by the iliac crest elevation and then scapulae elevation. This is due to the fact that a large PSIS-ASIS disparity is more inclined to cause an iliac crest and scapulae elevation. The natural reaction of this disparity may be an elevation of a hip opposite to the posterior hip as the pelvis tries to adjust for the lack of leverage on that posterior side.

Due to this reaction, the spine may react towards the posterior hip or away from the elevated hip. This may be a natural reaction in the thoracic spine or cervical spine to rebalance the head.

The measurement procedure generator 820 may determine the order of measurements for the frontal and sagittal plane 210 according to the greatest disparity or a predetermined order (see Appendix). The measurement procedure generator 820 may determine that the locomotor unit is the common denominator with these rules. If the locomotor unit is compensated, the measurement procedure generator 820 may cause reaction disparities from plane to plane and within the plane. For example, if there are any disparities in the locomotor unit, then the integrity of this foundational unit will more than likely cause an elevation of the iliac crest, which may cause the spine to shift laterally.

The posture health score generator 830 may determine the ratios of each of the measurements taken within a plane of symmetry to determine the order in which postural misalignments should be treated within the same plane of symmetry. The health score generator may emphasize some postural misalignments more than other postural misalignments. For example, if the PSIS/ASIS disparity scores a 9 (large), compared to a 6 (medium) at the iliac crest and six at the scapulae protraction, then more emphasis will be placed on the PSIS-ASIS as the ratio is 2:1:1 (see Appendix). Whatever the ratio determined, the health score generator is programmed to address these disparities within the plane in a similar manner as from plane to plane, making sure that the correct disparity is being addressed first followed by the others.

The posture health score generator 830 may determine that there is a 1:2:3 relationship between the Transverse, Frontal, and Sagittal plane 210 and the measurements involved (see Appendix). The health score generator may determine that the transverse plane 220 (as the only horizontal plane) will be the most sensitive to any type of disparity due to the attachments around this plane, and, therefore is weighted more heavily by the measurement procedure generator 820. The health score generator may also determine that the transverse plane 220 is the most compensated plane due to the fact that most people are one-side dominant. The health score generator may create a higher score for misalignments in this plane due to the increased likelihood of pelvic rotation misalignment, an elevated ilium, and knee rotation.

Referring to FIG. 9, illustrated is a posture health score chart 900 providing a posture health score for each of the planes of symmetry based on the measurements taken using the plane alignment laser tool 120 and the plane alignment measurer 110. The posture health score may isolate the planes of symmetry by score. Generating a score for each of the planes of symmetry identifies which plane would be optimal to begin exercising or working on.

The posture health score generator 830 may generate a posture health score for the traverse plane using one or more measurements. For example, the posture health score for the transverse plane may be based on PSIS-ASIS measurements, Iliac crest measurements, and scapula elevation measurements (see Appendix). The posture health score generator 830 may determine the score using the measurements by determining that the measurement falls between a minimum value and a maximum value in a range. Each range may correspond to a single score used to calculate the posture health score in the posture health score chart 900.

The posture health score generator 830 may generate a posture health score for the frontal plane using one or more measurements. For example, the posture health score for the frontal plane may be based on pelvic rotation measurements, torso rotation measurements, forward displacement pelvis measurements, forward displacement head measurements, forward displacement shoulder measurements, and scapular protraction left measurements (see Appendix). The posture health score generator 830 may determine the score using the measurements by determining that the measurement falls between a minimum value and a maximum value in a range. Each range may correspond to a single score used to calculate the posture health score in the posture health score chart 900.

The posture health score generator 830 may generate a posture health score for the sagittal plane using one or more measurements. For example, the posture health score for the sagittal plane may be based on spinal offset cervical measurements, spinal offset thoracic measurements, spinal offset lumbar measurements, legs internal/external measurements, legs valgus/varus measurements, feet everted/inverted left, and feet everted/inverted right. (see Appendix). The posture health score generator 830 may determine the score using the measurements by determining that the measurement falls between a minimum value and a maximum value in a range. Each range may correspond to a single score used to calculate the posture health score in the posture health score chart 900.

The posture health score may determine whether the patient has limited performance in the frontal plane 230, the transverse plane 220, or the sagittal plane 210 based on the transverse plane 220 measurements, the frontal plane 230 measurements, and the sagittal plane 210 measurements. The posture health score may first determine whether the transverse plane 220 measurements, frontal plane 230 measurements, and the sagittal plane 210 measurements affect any rotational, lateral, or medial movement. For example, if one has an elevated ilium, then a deviation from the transverse plane 220 may be measured. In some embodiments, a static postural misalignment may compromise the dynamic movement of that plane of symmetry. The posture health score considers the dynamic movements that are limited based on the static postural misalignments. The posture health score predicts movement limitations and goes beyond traditional therapies that primarily focus on rehabilitating weak muscles.

In some embodiments, a report may be generated that has an overall scale of 0 points to 81 points, higher being worse. The score may indicate the amount of pain or discomfort a person is in. In some embodiments, no pain is felt with a score lower than 40. With a score between 40 and 50, the patient may feel some periodic discomfort. With a score of 50 and higher, the patient is usually in some type of chronic pain, higher being more intense. The score may be referred to as the "structural score" and may also determine their risk factor for potentially being in pain if they aren't already in pain.

In some embodiments, the posture health score may determine the types of exercise in the rehabilitation routine and the progression of a rehabilitation routine. For example, with a score of 50 or higher, the end position may be supine, and the entire routine may have the patient on their back. With a score of 47 to 49, the routine starts in a supine position and slowly ramps up to a prone position to end the routine. With a score of 44 to 46, the routine starts in a supine position and slowly ramps up to a hand and knees position to end the routine. With a score of 41 to 43, the routine starts in a supine position and slowly ramps up to a kneeling position to end the routine. With a score of 37 to 39, the routine may start with the supine position and slowly ramp up to a sitting position to end the routine. With a score of 36 or lower, the routine starts with a supine position and slowly ramps up to a standing position to end the routine.

Referring to FIG. 10, illustrates a flowchart for prescribing a rehabilitation routine using the posture measurement data system.

At 1002, the routine generator 135 may select 12 corrective exercises for a routine. The routine generator 135 may apply factors for selecting an exercise. For example, the routine generator 135 may select exercises to allow for more flow from plane to plane and within each plane.

At 1004, the routine generator 135 may address the plane with the higher score and generates more exercises for routines addressing the affected plane of symmetry. The routine generator 135 may address the greatest measured disparity within that plane and may assign at least three exercises to make sure that disparity is addressed.

At 1006, the routine generator 135 may select two to three exercises for the remaining disparities that are of priority within the same plane. The routine generator 135 may repeat the same process for the two other planes and keep the number of exercises the same per plane or decrease the number of exercises in the subsequently prescribed planes.

At 1008, the routine generator 135 may schedule transition routines at or near transitions between movements that focus on two different planes of symmetry. The transition routine may primarily affect one plane of symmetry and also secondarily affect another plane of symmetry that the next set of exercises will focus on. For example, if the routine generator 135 is prescribing routines in the transverse plane 220 and is about to prescribe routines in the frontal plane 230, the routine generator 135 may pick a transverse plane 220 routine that secondarily affects the frontal plane 230.

At 1010, the routine generator 135 may re-generate routines every two weeks based on patient data from the user record system 145. This may mean that once the routine generator 135 generates a routine for a specific corrective sequence, the routine may be performed by the patient for the following two weeks. Following the two weeks, the routine generator 135 will generate new routines in response to posture realignment or the detection of new misalignments in the body due to the posture realignment.

At 1012, the routine generator 135 may select a short routine that covers the most important disparities in each plane. The short routine is an option if the client does not have the time to do the entire routine.

The routine generator 135 may prescribe corrective exercises in the early phase of rehabilitation and strength exercises in later phases of rehabilitation. The routine generator 135 may prescribe unilateral exercises followed by a bilateral exercise. For some patients, it may be necessary to reconfigure the neurological stimulus after a unilateral exercise to ensure the integrity of symmetry within the body. The routine generator 135 may prescribe unilateral exercises initially used more for correction, such as PSIS-ASIS disparities in the transverse plane 220. The routine generator 135 may address a specific disparity individually and then tie the movement resolving the disparity with a bilateral exercise. For example, the routine generator 135 may prescribe leg rotations with bent legs followed by hip rotations against the wall. The routine generator 135 may prescribe past routines after performing a new set of routines.

The routine generator 135 may prescribe passive exercises, isometric exercises, or active isometric exercises. A passive exercise requires no movement. Examples include a static floor or wall groin stretch. This would be considered a static stretching exercise where the body is positioned on the floor using multiple reference points to allow the weight of the body to act upon a joint. An isometric exercise may be a corrective exercise that provides work without movement and describes most of the Symmetry Postures. These exercises can include more isometric stretching, such as the Piriformis Crossovers or strengthening, such as the regular Piriformis Stretch. Isometric exercises may be considered the most appropriate for changing postural misalignment because they most directly influence the intrinsic musculature because intrinsic muscles do not change length with external force. An active isometric exercise may be a corrective exercise that provides specific movement of a joint or joints of an isometric holding position and does not displace the body over a measurable distance. For example, Hip Rotation (Wall), Shoulder Rotations, and Inverted Rotations are examples of Transverse plane 220 active isometric exercises. These exercises are also focused on correcting misalignment, but also add a slight strengthening component due to the movement. These exercises use multiple reference points to position the body at right angles to recruit a bilateral engagement or specific joint movement.

The routine generator 135 may prescribe strength exercises. The strength exercise may relate to the overall work being done in a position, and usually includes the engagement of two or more joints or large muscle groups. They can be categorized into two types: dynamic isometric and dynamic active. Dynamic Isometric may be an exercise that holds a specific position, usually involving more than two joints and in a load-bearing position. A sample of this would be the Wall Sit. Dynamic Active may be an exercise that displaces the body over a measurable distance and involves more than one joint. They are designed to strengthen the dynamic muscles to secure an aligned posture. Examples of this would be Pushups-walking out, Inchworms and Duck Walks.

Figure 11:
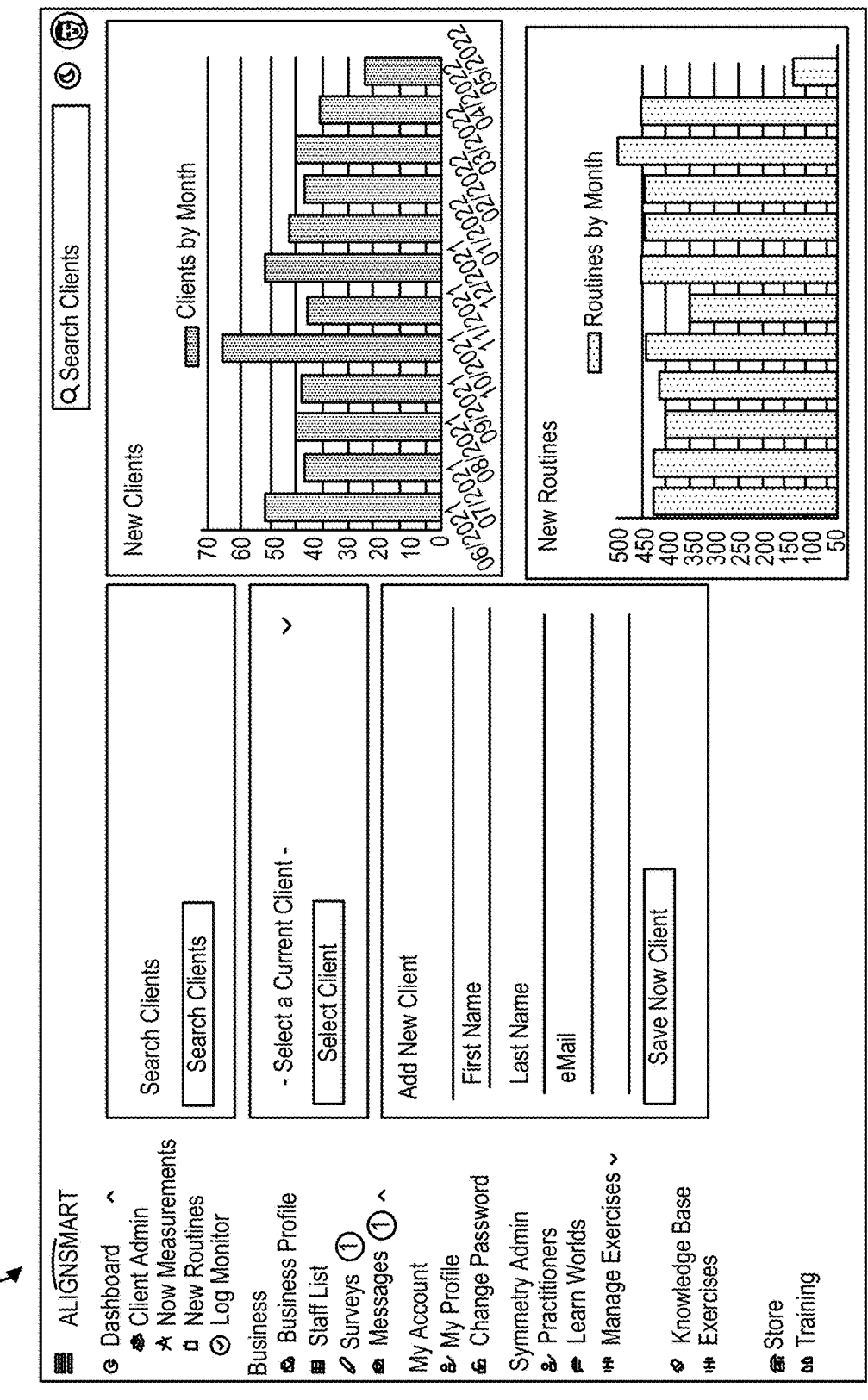
FIG. 11 depicts an example of a user interface generated by the posture measurement data system.

Referring to FIG. 11, illustrated is a user interface 1100 generated by the posture measurement data system. The user interface 1100 may be at a computer, a mobile device, and/or the like. The user interface 1100 may include a touchscreen. The posture measurement data system 130 may be communicatively coupled to the user interface 1100. The user interface 1100 may display program modes and user sessions of the rehabilitation routine.

The posture measurement data system 130 may be configured to present a notification via a user interface 1100 based on completing the rehabilitation routine. The posture measurement data system 130 may be configured to present a notification via a user interface 1100 based on the updated progress of the patient. The posture measurement data system 130 may present an exercise tutorial for the user to perform the exercise via the user interface 1100. The posture measurement data system 130 may present a counter to track the number of repetitions performed by the user via the user interface 1100. The posture measurement data system 130 may present a history log to display the number of days in which the rehabilitation routine was completed. The posture measurement data system 130 may present a selectable option to determine the type of exercise to be performed. The posture measurement data system 130 may present how an exercise is performed. The posture measurement data system 130 may present a prompt to inform the user that it is time to perform the rehabilitation routine.

The postural measurement data system may display multi-patient progress at the user interface 1100. The posture measurement data system 130 may be configured to present progress with respect to the improved postural realignment and decreased deviation from a plane of symmetry via the user interface 1100. For example, the posture measurement data system 130 may present the largest deviation from the plane of symmetry and the smallest deviation from the plane of symmetry measured by the posture alignment measurer and the plane alignment laser tool 120. In another example, the posture measurement data system 130 may present a graph of the measured angles of deviation over time. The posture measurement data system 130 may be configured to present progress for various exercises. For example, the posture measurement data system 130 may present a selectable option to enable the user to view progress of patients who perform exercises aimed to improve the sagittal plane 210. Additionally, the posture measurement data system 130 may generate an exercise program based on the user progress. For example, the posture measurement data system 130 may generate a more strenuous program for users who have shown progress over the past 10 days. The posture measurement data system 130 may be configured to present details of user performance from previous user sessions.

The posture measurement data system 130 may be configured to gather data related to patient progress via a user interface 1100. The posture measurement data system 130 may be configured to present questions and receive user responses related to user pain, user tightness, and user activities to measure progress related to the patient posture. Additionally, the posture measurement data system 130 may generate an exercise program based on the user responses. For example, the posture measurement data system 130 may generate a less strenuous program for users who are unable to perform certain exercises.

Referring to FIG. 12, illustrated is an example of a flowchart for generating and updating a rehabilitation routine using measurements from the plane alignment measurer 110 and the plane alignment laser tool 120. The posture measurement data system 130 may include a plane alignment measurer 110 having at least two arms and an angle sensor with the at least two arms configured to be placed on a patient. The angle sensor may be configured to determine a first posture angle at which the patient is tilted relative to a first plane of symmetry. The posture measurement data system may also include a plane alignment laser tool 120 at least two arms and a laser configured to generate focused light. The at least two arms are configured to be placed on the patient and the focused light from the laser is used to determine a second posture angle at which the patient is tilted relative to a second plane of symmetry.

At 1202, the posture measurement data system may determine a first posture angle relative to a plane of symmetry using a plane alignment measurer 110. The plane alignment measurer 110 may be flexible to allow the arms to be held flush against the portion of the patient body. The ends of the arms may be held flush against the portion of the patient body. The plane alignment measurer 110 may be placed on a portion of the patient body where the center body of the plane alignment measurer 110 aligns with a plane. That is, the arms may be positioned to align with anatomical landmarks on the patient. The angle sensor may include at least one of an accelerometer or a gyroscope. The gyroscope and/or accelerometer may determine the angle at which the arms are tilted relative of the central body 320. The transmitter may be configured to communicatively couple to the posture measurement data system. The transmitter may be configured to transmit the deviation angles from one of the planes to the posture measurement data system. The plane alignment measurer 110 may also be configured to receive a prompt for presentation from the posture measurement data system. The posture measurement data system may be configured to determine a third postural angle is needed from the plane alignment measurer 110. The posture measurement data system may be configured to generate a prompt for presentation to an operator of the plane alignment measurer 110 to take the third postural angle using the plane alignment measurer 110. The posture measurement data system may be configured to update a postural health score in response to receiving the third postural angle. The posture measurement data system may be configured to generate the rehabilitation routine based on the postural health score, the first posture angle, and the second posture angle.

At 1204, the posture measurement data system may determine a second posture angle relative to a second plane of symmetry using the plane alignment laser tool 120. The plane alignment laser tool 120 may include a laser configured to project focused light outward from the housing 350. The focused light may be channeled into a line. In some embodiments, a mat 600 is included having a first side with a range of angles 610 and a second side having crosshairs 630. The mat 600 may be configured to lay flat to allow the patient to stand on the mat 600 with a plane of symmetry aligned with the crosshairs 630. The second posture angle may be determined by aligning the line of focused light from the laser onto the range of angles 610 while the line is passing through the crosshairs 630.

At 1206, the posture measurement data system 130 may generate a rehabilitation routine based on the first posture angle and the second posture angle. The ordering of the rehabilitation routine may be determined based upon a severity of misalignments with respect to the first plane of symmetry and the second plane of symmetry. In some embodiments, the posture measurement data system 130 may calculate a difference between the first posture angle and a first target posture angle, the first target posture angle being an ideal angle that the patient would be aligned with relative to the first plane of symmetry. The posture measurement data system may select a rehabilitative exercise to be performed in a supine position in response to the difference satisfying a misalignment threshold where the rehabilitative exercise to be included in the rehabilitation routine. The second posture angle may be determined by aligning the line of focused light from the laser onto the range of angles 610 while the line is passing through the crosshairs 630. The posture measurement data system may determine a first postural health score based on at least the first postural angle and a second postural health score based on the second posture angle. The posture measurement data system may adjust a weighting ratio applied to the first postural health score and the second postural health score in response to determining that the first postural health score corresponding to the first plane of symmetry satisfies a misalignment threshold. The posture measurement data system may determine that a first set of rehabilitative exercises are to be added first to the routine based on the first postural health score being more severe than the second postural health score where the second postural health score was higher than the first postural health score prior to the weighting ratio being adjusted. The posture measurement data system may generate the first set of rehabilitative exercises corresponding to the first plane of symmetry and a second set of rehabilitative exercises corresponding to the second plane of symmetry in response to adjusting the weighting ratio applied to first postural health score and the second postural health score.

At 1208, the posture measurement data system 130 may transmit the rehabilitation routine to a client device 160. The posture measurement data system 130 may transmit the alert in response to determining that the supply container is en route to the patient terminal 240 or has arrived at the patient terminal 240. In some embodiment, the alerts may include messages containing information about patients, medications for the patients, and locations of the patients. The client device 160 may be configured to display a user interface 1100 for tracking goals and progress with the rehabilitation routine. In some embodiments, the posture measurement data system may be configured to generate the user interface 1100 for presentation on the client device 160. The posture measurement data system may add a new routine to the rehabilitation routine based on input from the client device 160, the input being indicative of an achieved goal and satisfactory progress with the rehabilitation routine.

At 1210, the posture measurement data system 130 may update the rehabilitation routine based on the user performance data from the client device 160. The plane alignment measurer 110 includes a transmitter communicatively coupled to the controller, and wherein the controller is further configured to receive the first posture angle transmitted by the plane alignment measurer 110. The posture measurement data system may calculate a difference between the first posture angle and a first target posture angle, the first target posture angle being an ideal angle that the patient would be aligned with relative to the first plane of symmetry. The posture measurement data system may determine the difference is less than a previously measured difference between a past posture angle and the first target posture angle. The posture measurement data system may adjust the rehabilitation routine based on the difference between the first posture angle and the first target posture angle in response to the difference being less than the previously measured difference between the past posture angle and the first target posture angle.

Referring to FIG. 13, the computing system 1300 may include a processor 1310, a memory 1320, a storage device 1330, and an input/output device 1340. The processor 1310, the memory 1320, the storage device 1330, and the input/output device 1340 may be interconnected via a system bus 1350. The processor 1310 is capable of processing instructions for execution within the computing system 1300. Such executed instructions may implement one or more components of, for example, hardware for posture measurement systems for realignment. In some exemplary embodiments, the processor 1310 may be a single-threaded processor. Alternately, the processor 1310 may be a multi-threaded processor. The processor 1310 is capable of processing instructions stored in the memory 1320 and/or on the storage device 1330 to display graphical information for a user interface provided via the input/output device 1340.

The memory 1320 is a non-transitory computer-readable medium that stores information within the computing system 1300. The memory 1320 may be configured to store data structures representing configuration object databases, for example. The storage device 1330 is capable of providing persistent storage for the computing system 1300. The storage device 1330 may be a floppy disk device, a hard disk device, an optical disk device, or a tape device, or other suitable persistent storage means. The input/output device 1340 provides input/output operations for the computing system 1300. In some exemplary embodiments, the input/output device 1340 includes a keyboard and/or pointing device. In various implementations, the input/output device 1340 includes a display unit for displaying graphical user interfaces.

According to some exemplary embodiments, the input/output device 1340 may provide input/output operations for a network device. For example, the input/output device 1340 may include Ethernet ports or other networking ports to communicate with one or more wired and/or wireless networks (e.g., a local area network (LAN), a wide area network (WAN), the Internet, a public land mobile network (PLMN), and/or the like).

In some exemplary embodiments, the computing system 1300 may be used to execute various interactive computer software applications that may be used for organization, analysis, and/or storage of data in various formats. Alternatively, the computing system 1300 may be used to execute any type of software application. These applications may be used to perform various functionalities, e.g., planning functionalities (e.g., generating, managing, editing of spreadsheet documents, word processing documents, and/or any other objects, etc.), computing functionalities, communications functionalities, etc. The applications may include various add-in functionalities or may be standalone computing items and/or functionalities. Upon activation within the applications, the functionalities may be used to generate the user interface provided via the input/output device 1340. The user interface may be generated and presented to a user by the computing system 1300 (e.g., on a computer screen monitor, etc.).

Terminology used herein is for the purpose of describing particular embodiments only and is not intended to be limiting of the embodiments. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" may be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

While the foregoing is directed to implementations of the present disclosure, other and further implementations of the disclosure may be devised without departing from the basic scope thereof, and the scope thereof is determined by the claims that follow.

What is claimed is:

1. A system comprising:
a plane alignment measurer having at least two arms and an angle sensor, the at least two arms configured to be placed on a patient, the angle sensor configured to determine a first posture angle at which the patient is tilted relative to a first plane of symmetry;
a plane alignment laser tool having at least two arms and a laser configured to generate focused light, the at least two arms configured to be placed on the patient, the focused light from the laser being used to determine a second posture angle at which the patient is tilted relative to a second plane of symmetry, the second plane of symmetry being different from the first plane of symmetry; and
a controller configured to:
generate a rehabilitation routine based on the first posture angle relative to the first plane of symmetry and the second posture angle relative to the second plane of symmetry, the first posture angle obtained using the plane alignment measurer, the second posture angle obtained using the plane alignment laser tool, the rehabilitation routine for correcting posture misalignments.

2. The system of claim 1, wherein the plane alignment measurer includes a transmitter communicatively coupled to the controller, and wherein the controller is further configured to receive the first posture angle transmitted by the plane alignment measurer.

3. The system of claim 1, wherein the angle sensor includes at least one of an accelerometer or a gyroscope and wherein the arms are positioned to align with anatomical landmarks on the patient.

4. The system of claim 1, wherein the controller is further configured to:
calculate a difference between the first posture angle and a first target posture angle, the first target posture angle being an ideal angle that the patient would be aligned with relative to the first plane of symmetry; and
select a rehabilitative exercise to be performed in a supine position in response to the difference satisfying a misalignment threshold, the rehabilitative exercise to be included in the rehabilitation routine.

5. The system of claim 1, wherein the controller is further configured to:
calculate a difference between the first posture angle and a first target posture angle, the first target posture angle being an ideal angle that the patient would be aligned with relative to the first plane of symmetry; and
determine the difference is less than a previously measured difference between a past posture angle and the first target posture angle; and
in response to the difference being less than the previously measured difference between the past posture angle and the first target posture angle, adjust the rehabilitation routine based on the difference between the first posture angle and the first target posture angle.

6. The system of claim 1, further comprising:
a mat having a first side and a second side, the first side of the mat having a range of angles and the second side having crosshairs, the mat being configured to lay flat to allow the patient to stand on the mat with a plane of symmetry aligned with the crosshairs,
wherein the plane alignment laser tool is further configured to focus light onto the mat in a line of focused light, and
wherein the second posture angle is determined by aligning the line of focused light from the laser onto the range of angles while the line is passing through the crosshairs.

7. The system of claim 1, further comprising:
a client device configured to display a user interface for tracking goals and progress with the rehabilitation routine,
wherein the controller is further configured to:
generate the user interface for presentation on the client device; and add a new routine to the rehabilitation routine based on input from the client device, the input being indicative of an achieved goal and satisfactory progress with the rehabilitation routine.

8. The system of claim 1, wherein the controller is further configured to:

determine that a third postural angle is needed from the plane alignment measurer;

generate a prompt for presentation to an operator of the plane alignment measurer to take the third postural angle using the plane alignment measurer;

update a postural health score in response to receiving the third postural angle; and generate the rehabilitation routine based on the postural health score, the first posture angle, and the second posture angle.

9. The system of claim 1, wherein an ordering of the rehabilitation routine is determined based upon a severity of misalignments with respect to the first plane of symmetry and the second plane of symmetry.

10. The system of claim 1, wherein the controller is further configured to:

determine a first postural health score based on at least the first postural angle and a second postural health score based on the second posture angle;

in response to determining that the first postural health score corresponding to the first plane of symmetry satisfies a misalignment threshold, adjust a weighting ratio applied to the first postural health score and the second postural health score;

in response to adjusting the weighting ratio applied to first postural health score and the second postural health score, determine that a first set of rehabilitative exercises are to be added first to the routine based on the first postural health score being more severe than the second postural health score, the second postural health score being higher than the first postural health score prior to the weighting ratio being adjusted, the first set of rehabilitative exercises corresponding to the first plane of symmetry and a second set of rehabilitative exercises corresponding to the second plane of symmetry; and generate the rehabilitation routine with the first set of rehabilitative exercises to be performed before the second set of rehabilitative exercises.

11. A system comprising:

a plane alignment measurer having at least two arms and an angle sensor, the at least two arms configured to be placed on a patient, the angle sensor configured to determine a first posture angle at which the patient is tilted relative to a first plane of symmetry;

a plane alignment laser tool having at least two arms and a laser configured to generate focused light, the at least two arms configured to be placed on the patient, the focused light from the laser being used to determine a second posture angle at which the patient is tilted relative to a second plane of symmetry, the second plane of symmetry being different from the first plane of symmetry; and a server configured to:

generate a rehabilitation routine based on the first posture angle relative to the first plane of symmetry and the second posture angle relative to the second plane of symmetry, the first posture angle obtained using the plane alignment measurer, the second posture angle obtained using the plane alignment laser tool, the rehabilitation routine for correcting posture misalignments.

12. The system of claim 11, wherein the plane alignment measurer includes a transmitter communicatively coupled to the server, and wherein the server is further configured to receive the first posture angle transmitted by the plane alignment measurer.

13. The system of claim 11, wherein the angle sensor includes at least one of an accelerometer or a gyroscope and wherein the arms are positioned to align with anatomical landmarks on the patient.

14. The system of claim 11, wherein the server is further configured to:

calculate a difference between the first posture angle and a first target posture angle, the first target posture angle being an ideal angle that the patient would be aligned with relative to the first plane of symmetry; and select a rehabilitative exercise to be performed in a supine position in response to the difference satisfying a misalignment threshold, the rehabilitative exercise to be included in the rehabilitation routine.

15. The system of claim 11, wherein the server is further configured to:

calculate a difference between the first posture angle and a first target posture angle, the first target posture angle being an ideal angle that the patient would be aligned with relative to the first plane of symmetry; and determining the difference is less than a previously measured difference between a past posture angle and the first target posture angle; and in response to the difference being less than the previously measured difference between the past posture angle and the first target posture angle, adjusting the rehabilitation routine based on the difference between the first posture angle and the first target posture angle.

16. The system of claim 11, further comprising:

a mat having a first side and a second side, the first side of the mat having a range of angles and the second side having crosshairs, the mat being configured to lay flat to allow the patient to stand on the mat with a plane of symmetry aligned with the crosshairs, wherein the plane alignment laser tool is further configured to focus light onto the mat in a line of focused light, and wherein the second posture angle is determined by aligning the line of focused light from the laser onto the range of angles while the line is passing through the crosshairs.

17. The system of claim 11, further comprising:

a client device configured to display a user interface for tracking goals and progress with the rehabilitation routine, wherein the server is further configured to:

generating the user interface for presentation on the client device; and adding a new routine to the rehabilitation routine based on input from the client device, the input being indicative of an achieved goal and satisfactory progress with the rehabilitation routine.

18. The system of claim 11, wherein the server is further configured to:

determine that a third postural angle is needed from the plane alignment measurer;

generate a prompt for presentation to an operator of the plane alignment measurer to take the third postural angle using the plane alignment measurer;

update a postural health score in response to receiving the third postural angle; and generate the rehabilitation routine based on the postural health score, the first posture angle, and the second posture angle.

19. The system of claim 11, wherein an ordering of the rehabilitation routine is determined based upon a severity of misalignments with respect to the first plane of symmetry and the second plane of symmetry.

20. The system of claim 11, wherein the server is further configured to:

determining a first postural health score based on at least the first postural angle and a second postural health score based on the second posture angle;

in response to determining that the first postural health score corresponding to the first plane of symmetry satisfies a misalignment threshold, adjusting a weight- ing ratio applied to the first postural health score and the second postural health score;

in response to adjusting the weighting ratio applied to first postural health score and the second postural health score, determining that a first set of rehabilitative exercises are to be added first to the routine based on the first postural health score being more severe than the second postural health score, the second postural health score being higher than the first postural health score prior to the weighting ratio being adjusted, the first set of rehabilitative exercises corresponding to the first plane of symmetry and a second set of rehabilita- tive exercises corresponding to the second plane of symmetry; and generating the rehabilitation routine with the first set of rehabilitative exercises to be performed before the second set of rehabilitative exercises.

* * * * *